(12) United States Patent
McEntire et al.

(10) Patent No.: US 12,239,761 B2
(45) Date of Patent: *Mar. 4, 2025

(54) METHODS OF SILICON NITRIDE LASER CLADDING

(71) Applicant: SINTX TECHNOLOGIES, INC., Salt Lake City, UT (US)

(72) Inventors: Bryan J. McEntire, Salt Lake City, UT (US); Bhajanjit Singh Bal, Salt Lake City, UT (US); Ryan M. Bock, Salt Lake City, UT (US)

(73) Assignee: SINTX Technologies, Inc., Salt Lake City, UT (US)

( * ) Notice: Subject to any disclaimer, the term of this patent is extended or adjusted under 35 U.S.C. 154(b) by 788 days.

This patent is subject to a terminal disclaimer.

(21) Appl. No.: 17/237,687

(22) Filed: Apr. 22, 2021

(65) Prior Publication Data

US 2021/0330860 A1   Oct. 28, 2021

Related U.S. Application Data

(60) Provisional application No. 63/014,235, filed on Apr. 23, 2020.

(51) Int. Cl.
| | | |
|---|---|---|
| *C23C 24/00* | (2006.01) | |
| *A61L 27/30* | (2006.01) | |
| *A61L 27/54* | (2006.01) | |
| *B23K 26/0622* | (2014.01) | |
| *B23K 26/12* | (2014.01) | |
| *B23K 26/324* | (2014.01) | |
| *B23K 26/60* | (2014.01) | |

(Continued)

(52) U.S. Cl.
CPC ............. *A61L 27/306* (2013.01); *A61L 27/54* (2013.01); *B23K 26/0624* (2015.10); *B23K 26/123* (2013.01); *B23K 26/324* (2013.01); *B23K 26/60* (2015.10); *C22C 14/00* (2013.01); *C23C 26/00* (2013.01); *A61L 2300/412* (2013.01); *A61L 2420/02* (2013.01); *A61L 2430/02* (2013.01)

(58) Field of Classification Search
CPC ..................................................... C23C 24/00
See application file for complete search history.

(56) References Cited

U.S. PATENT DOCUMENTS

| | | |
|---|---|---|
| 5,057,335 A | 10/1991 | Hanagata et al. |
| 2004/0228963 A1 | 11/2004 | Bergh et al. |
| 2010/0047434 A1 | 2/2010 | Kumar |

(Continued)

FOREIGN PATENT DOCUMENTS

CN       108516871 A       9/2018

OTHER PUBLICATIONS

Zanocco et al. 3-D additive deposition of an antibacterial and osteogenic silicon nitride coating on orthopaedic titanium substrate. Journal of the Mechanical Behavior of Biomedical Materials. 103. Nov. 2019 (Year: 2019).*

(Continued)

*Primary Examiner* — Cachet I Proctor
(74) *Attorney, Agent, or Firm* — Polsinelli PC

(57) ABSTRACT

Disclosed herein are methods for laser cladding a coating the surface of a biomedical implant. The biomedical implant may be an implant with a laser-cladded silicon nitride coating for promoting osteogenesis.

21 Claims, 41 Drawing Sheets
(40 of 41 Drawing Sheet(s) Filed in Color)

(51) Int. Cl.
    C22C 14/00    (2006.01)
    C23C 26/00    (2006.01)

(56) References Cited

U.S. PATENT DOCUMENTS

2014/0277571 A1* 9/2014 Pettersson ............ A61L 27/10
                                              204/192.15
2016/0339144 A1* 11/2016 McEntire ............ A61L 27/446
2017/0197014 A1* 7/2017 McEntire ............ A61L 27/06

OTHER PUBLICATIONS

Xu et al. Laser Cladding of Composite Bioceramic Coatings on Titanium Alloy. Journal of Materials Engineering and Performance. Vo.. 25 (2) pp. 656-667. Feb. 2016 (Year: 2016).*

Marin et al. Silicon nitride laser cladding: A feasible technique to improve the biological response of zirconia. Materials and Design. 191. Mar. 2020 (Year: 2020).*

Soltani et al. Laser ablation mechanism of silicon nitride with nanosecond and picsecond lasers. Optics and Laser Technology. 119. Jul. 2019 (Year: 2019).*

International Search Report and Written Opinion from corresponding Application No. PCT/US021-028641, issued Aug. 13, 2021, 7 pages.

Marin et al., Silicon nitride laser cladding: A feasible technique to improve the biological response of zirconia, Materials Design, Mar. 17, 2020; doi: 10.1016/j.jmatdes.2020. 108649.

Xu et al., Laser Cladding of Composite Bioceramic Coatings on Titanium Alloy, Journal of Materials Engineering and Performance, Feb. 2016; doi: 10.1007/s11665-015-1868-4.

Bhagavat et al., Effects of mixed abrasive slurries on free abrasive machining processes, Proceedings of the 2005 ASPE Conference, Citeseerx.ist.psu.edu/viewdoc/download?doi=10.1.1.510.9007&rep=rep1&type=pdf. 2015.

Zanocco, M. et al., "3D-additive deposition of an antibacterial and osteogenic silcon nitride coating on orthopaedic titanium substrate," Journal of the Mechanical Behavior of Biomedical Materials, vol. 103, Nov. 26, 2019, 11 pages.

European Patent Office, Extended European Search Report, Application No. 21792434.9, Nov. 29, 2023, 8 pages.

U.S Patent and Trademark Office, Non-Final Office Action, U.S. Appl. No. 17/239,412, filed Dec. 21, 2023, 6 pages.

China National Intellectual Property Administration, First Office Action, Application No. 202180030422.1, Apr. 4, 2024, 29 pages.

Vision Lasertechnik, LWI V WT Workstation, Mar. 25, 2018, retrieved from <http://web,archive.org/web/20180325054108/https://www.vision-lasertechnik.de/producUlwi-v-wU?lang=en>.

International Search Report and Written Opinion issued in corresponding Application No. PCT/US2021/028975 on Aug. 6, 2021, 7 pages.

* cited by examiner

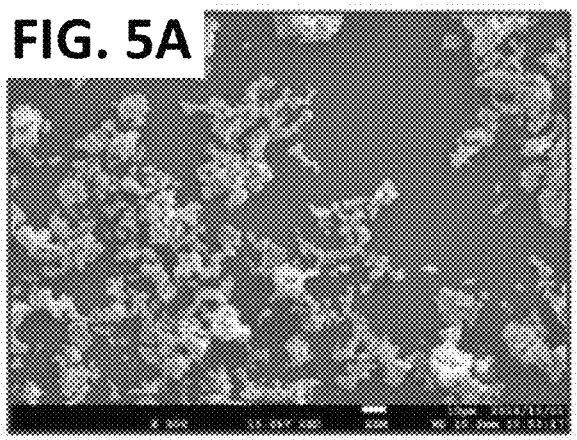
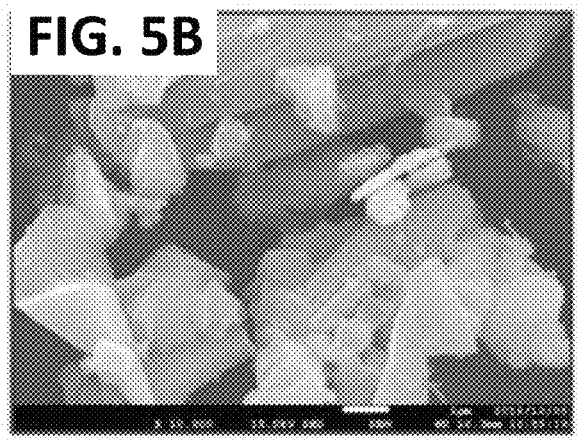
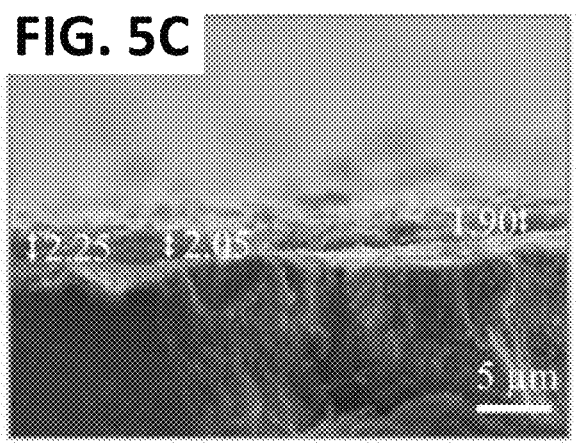
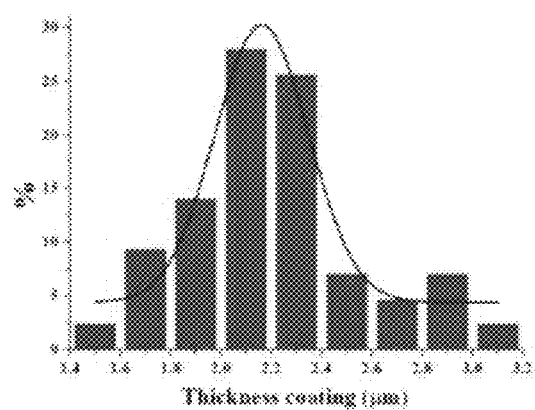
FIG. 5A
FIG. 5B
FIG. 5C
FIG. 5D

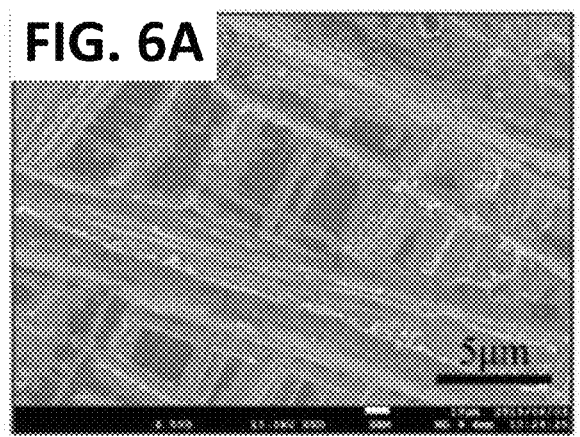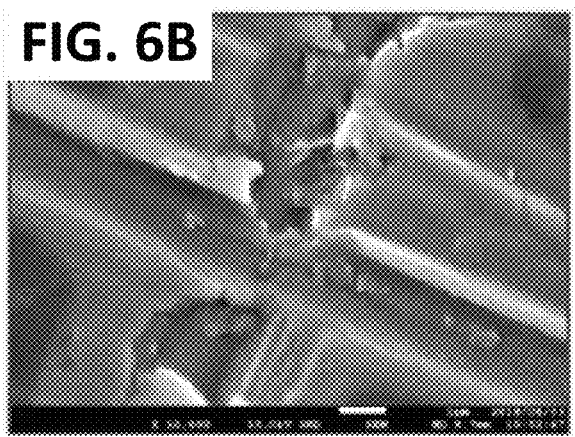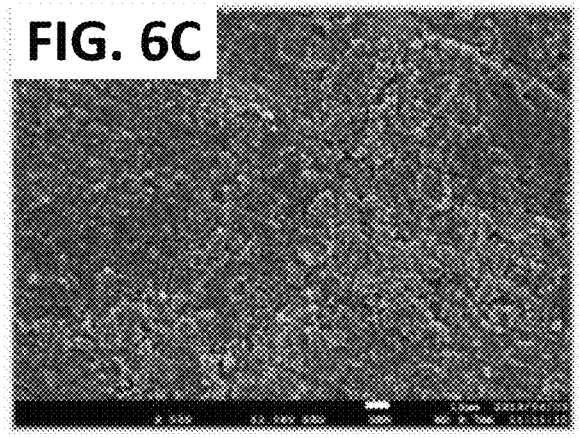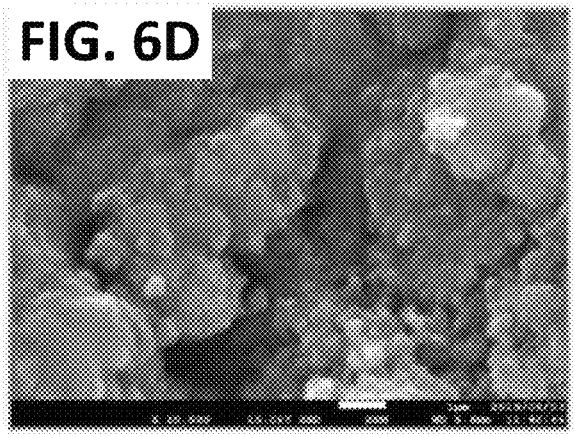

LDPE substrate

Ti6Al4V substrate

ZTA substrate

Y-TZP substrate

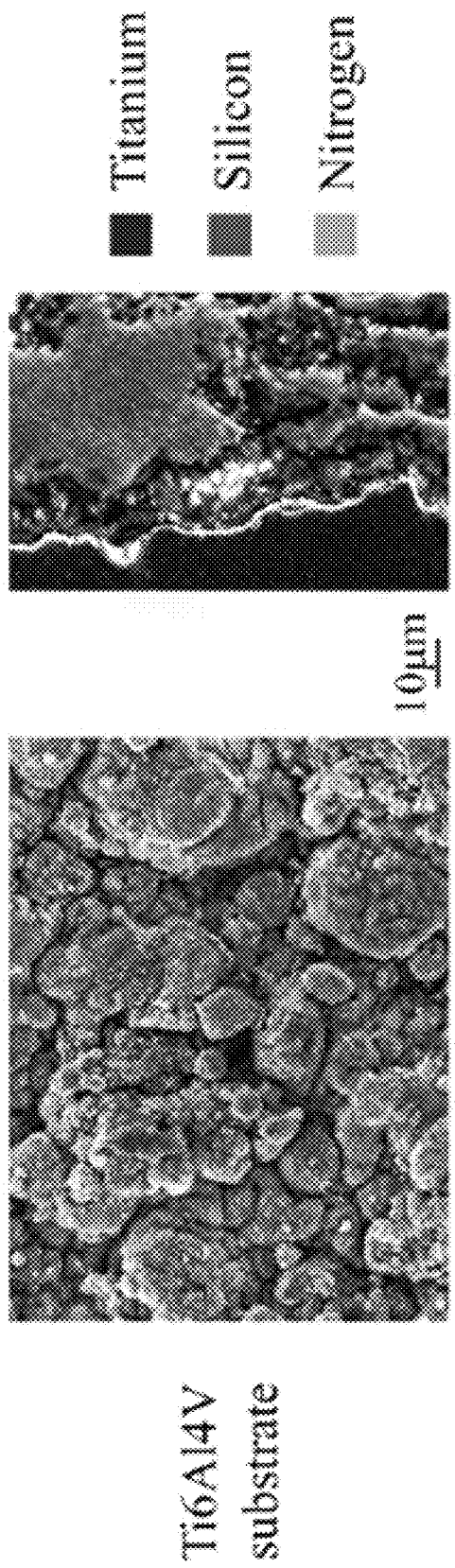

LDPE substrate

Si₃N₄ phase

Polyethylene substrate

Ti6Al4V substrate

Si₃N₄ phase

Blue amorphous phase
Green silicon phase

ZTA substrate

Blue amorphous phase
Green silicon phase

Si₃N₄ phase

Y-TZP substrate $* = p < 0.05$
$ns = not\ significant$

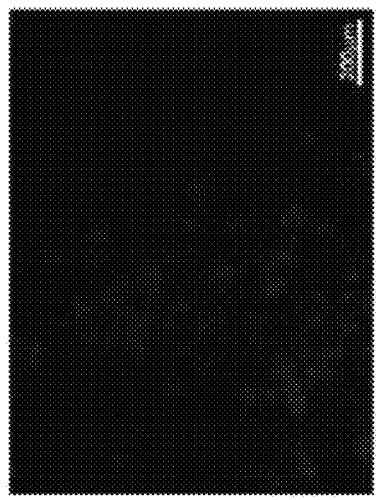
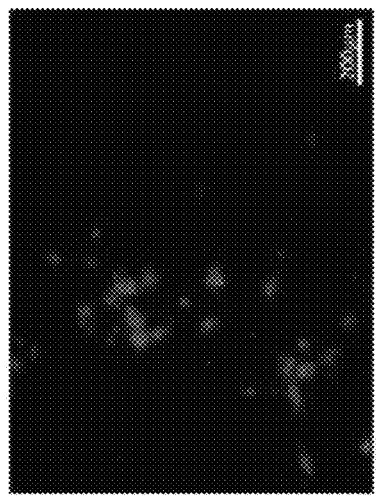
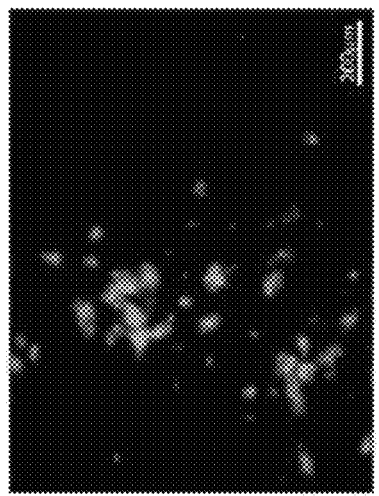
FIG. 25C
FIG. 25B
FIG. 25A

METHODS OF SILICON NITRIDE LASER CLADDING

CROSS-REFERENCE TO RELATED APPLICATIONS

This application claims priority to US Provisional Application No. 63/014,235; filed Apr. 23, 2020, the contents of which are entirely incorporated by reference herein.

FIELD

The present disclosure relates to systems and methods for silicon nitride laser cladding, and in particular to improving the biological response of zirconia using silicon nitride laser cladding.

BACKGROUND

Zirconium oxide or "zirconia" ($ZrO_2$) is the strongest among the ceramic biomaterials on the market for the fabrication of crowns and fixed partial dentures. Zirconia's natural white color and high mechanical properties make it the ideal candidate material for the production of resistant, esthetically attractive implants.

In the recent past, many concerns have been raised about the suitability of zirconia for biomedical applications, in particular after the catastrophic failure of a series of zirconia femoral heads manufactured in 2001; about 400 femoral heads failed over a short period due to an unexpected, accelerated ageing process caused by a small variation of the process parameters applied during sintering. The unexpected and unprecedented accident raised concerns about other $ZrO_2$ components; the ISO 13356 (1997) guidelines did not consider material aging at the time.

At room temperature, zirconia is only stable in its monoclinic form, which has relatively low mechanical properties. When heated above 1170° C., monoclinic zirconia transforms into the more compact tetragonal phase, which then inevitably disintegrates by cracking upon cooling. To maintain the integrity of sintered zirconia components, one can either sinter at low temperature, to obtain a fully monoclinic body, or stabilize the tetragonal phase by alloying, thereby avoiding the t-m transformation during cooling. The high fracture toughness exhibited by tetragonal zirconia at room temperature is associated with a stress-induced t→m transformation which inhibits crack propagation. However, zirconia's fracture toughness is still compromised by prolonged exposure to humid environments, a process referred to as low-temperature degradation (LTD).

Other than esthetics and mechanics, the success of dental implants is also determined by biocompatibility. Zirconia is considered an inert biomaterial, meaning that it has limited interactions with biological environments. In vitro and in vivo testing on zirconia showed no evidence for mutagenic or carcinogenic effects and a low affinity to bacterial plaque, but also limited adhesion to biological tissues, in particular bone. Many different treatments have been proposed in order to improve the biological activity of zirconia and promote its integration in existing biological tissues. These include alloying with active phases such as hydroxyapatite, coatings, surface laser modifications, and texturing.

Titanium is another common biomaterial. It is useful for various biomedical purposes such as total joint arthroplasty, traumatic and compound bone fractures, craniomaxillofacial, and dental implants. However, its ability to osseointegrate with human bone is also limited without first functionalizing its surface. Various functionalization methods have been developed. The most common is to first roughen the surface of the titanium implant using sandblasting and then subject it to acid etching. This process creates minute cavities in the surface of the metal that allow osteoblasts to initiate mineralization of the metal surface. Another method of functionalizing titanium is to flame-spray a coating of calcium phosphate or hydroxyapatite onto its surface. This is done for orthopaedic hip stems and acetabular cups in total joint arthroplasty. An additional functionalization method is to apply a coating of calcium phosphate or hydroxyapatite using physical or chemical vapor deposition. However, without appropriate functionalization, titanium does not effectively osseointegrate with native bone tissue. Titanium, like most all metals, can be allergenic or toxic to patients, and post-operative metallosis and pseudotumors are commonly reported in medical journals. Other implanted metals such as cobalt-chromium and stainless steel alloys have similar deficiencies.

Biopolymers are additional implant materials that have poor osseous integration characteristics. Polyethylene (PE), polyurethane (PU), polymethylmethacrylate (PMMA), polyetheretherketone (PEEK), and polyetherketoneketone (PEKK) are several polymers that require surface functionalization to integrate with native bone. Similar functionalization methods are used for these materials including surface roughening, acid etching, or coating them with titanium, calcium phosphate or hydroxyapatite. While surface roughening and acid etching are helpful in promoting osseous integration, their ability to do so is generally poorer than biometals; and due to the dissimilarity of the materials, coatings on polymers often fail via delamination at the interface between the coating and the polymer.

Therefore, there is a need for alternative surface functionalization of ceramics—including zirconia and zirconia toughened alumina, biometals—including titanium and titanium alloys, stainless steels, and cobalt-chromium alloys, and biopolymers—including polyethylene, polyurethane, polyetheretherketone, and polyetherketoneketone—to promote osteointegration.

SUMMARY

In an aspect, the present disclosure encompasses a method of laser cladding the surface of a biomedical implant. The method of coating the surface of a biomedical implant may include providing the biomedical implant, roughening at least one surface of the biomedical implant, laser cladding a coating of silicon nitride on the at least one roughened surface, and repeating the laser cladding step until the coating of silicon nitride has a thickness of at least 10 µm. In some aspects, the laser cladding may include directing a laser beam to at least one roughened surface of the biomedical implant, and pre-applying a powder mixture or simultaneously directing a powder mixture comprising silicon nitride powder to the at least one roughened surface of the biomedical implant. The laser cladding may be repeated at least three times, such that the coating of silicon nitride has a thickness of at least 15 µm. The laser cladding step may further include supplying a constant flux of nitrogen gas.

The biomedical implant may include zirconia, yttria-stabilized zirconia, alumina, alumina/zirconia composites (ZTA), titanium, titanium alloys, stainless steel, and cobalt chromium alloys, polyethylene, polyurethane, polyetheretherketone, and/or polyetherketoneketone. The coating of silicon nitride may include about 5 wt. % to about 15 wt. % silicon nitride. In some aspects, the silicon nitride powder may include $\alpha$-$Si_3N_4$, $\beta$-$Si_3N_4$, $\beta$-SiYAlON, SiAlON, or SiYON. The silicon nitride powder may be formed from ground acicular $\beta$-$Si_3N_4$ grains and a Si—Y—O—N grain-boundary phase. Roughening at least one surface of the biomedical implant may include using free abrasive machining or sandblasting to form random scratches that may be 5 to 500 μm wide.

Also provided here are methods of promoting osteogenesis. The method may include contacting the laser-cladded silicon nitride coated biomedical implant with living human tissue. In some aspects, bone tissue production increases on the biomedical implant as compared to an implant without the laser-cladded silicon nitride coating. Osteocalcin and osteopontin distributions may be increased on the biomedical implant as compared to an implant without the laser-cladded silicon nitride coating. The bone tissue may have a higher degree of osseous integration to the biomedical implant as compared to an implant without the laser-cladded silicon nitride coating. Mineralized tissue may increase on the biomedical implant as compared to an implant without the laser-cladded silicon nitride coating. There may be an increase in mineral hydroxyapatite on the biomedical implant as compared to an implant without the laser-cladded silicon nitride coating.

Further provided herein is a biomedical implant having a laser-cladded silicon nitride surface.

Other aspects and iterations of the invention are described more thoroughly below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate several embodiments of the invention and together with the description serve to explain the principles of the invention.

FIG. 5A shows $Si_3N_4$ powders observed by SEM at low magnification.

FIG. 5B shows $Si_3N_4$ powders observed by SEM at high magnification.

FIG. 5C is a cross sectional analysis shown in an isometric view.

FIG. 5D is a distribution of the powder equivalent diameter measured by SEM.

FIG. 6A is a scanning electron image of a roughened zirconia sample before laser cladding at low magnification.

FIG. 6B is a scanning electron image of a roughened zirconia sample before laser cladding at high magnification.

FIG. 6C is a scanning electron image of a roughened zirconia sample after laser cladding at low magnification.

FIG. 6D is a scanning electron image of a roughened zirconia sample after laser cladding at high magnification.

FIG. 17B shows a laser microscope substrate surface image of coated LDPE.

FIG. 18C shows a SEM secondary electron image overlapped with an EDS compositional maps for a Ti6Al4V surface analysis.

FIG. 18D shows a SEM secondary electron image overlapped with an EDS compositional maps for a Ti6Al4V cross-section analysis.

FIG. 25A is a fluorescence micrograph of a Ti6Al4V sample showing osteocalcin after exposure to SaOS-2 cells.

FIG. 25B is a fluorescence micrograph of a Ti6Al4V sample showing osteopontin after exposure to SaOS-2 cells.

FIG. 25C is a fluorescence micrograph of a Ti6Al4V sample showing nuclei after exposure to SaOS-2 cells.

DETAILED DESCRIPTION

Figure 1:
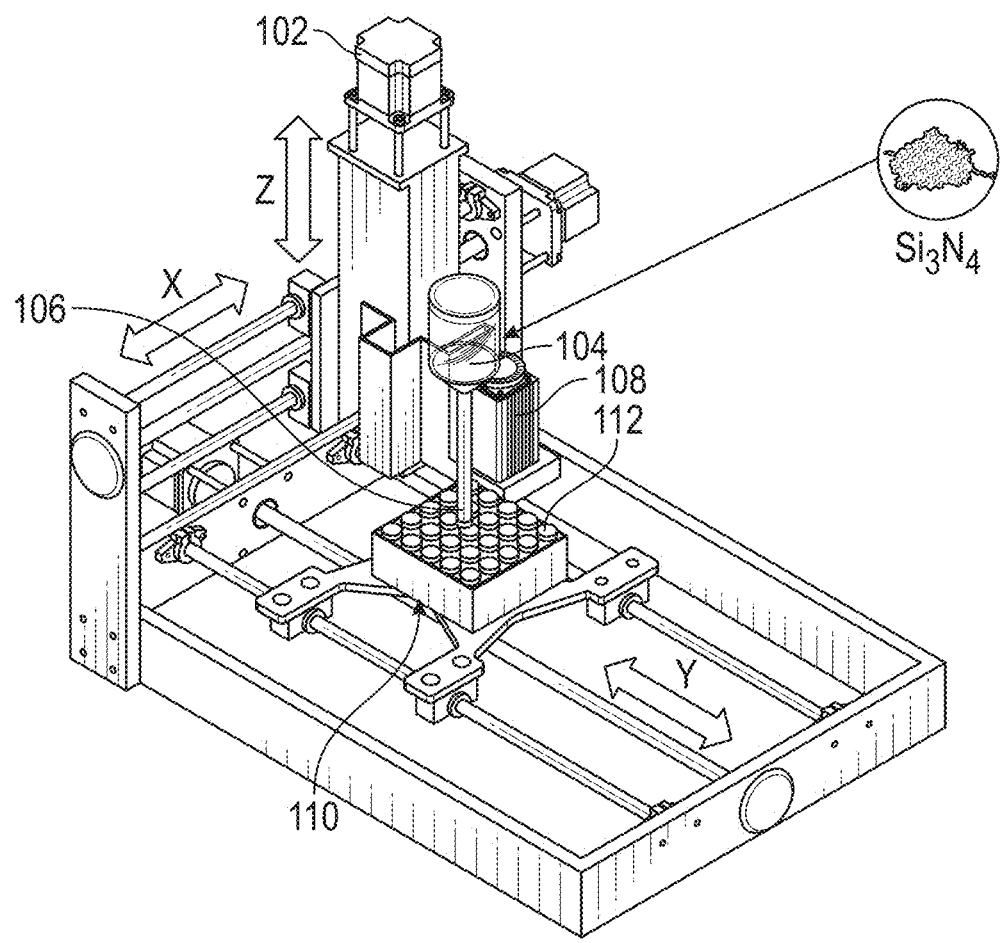
FIG. 1 is a schematic representation of the deposition process.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

As used herein, the terms "comprising," "having," and "including" are used in their open, non-limiting sense. The terms "a," "an," and "the" are understood to encompass the plural as well as the singular. Thus, the term "a mixture thereof" also relates to "mixtures thereof."

As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

As used herein, the term "silicon nitride" includes $Si_3N_4$, $\alpha$-$Si_3N_4$ or $\beta$-$Si_3N_4$, $\beta$-SiYAlON, SiYON, SiAlON, or combinations of these phases or materials.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

Provided herein are methods of laser cladding treatment with $Si_3N_4$ powders that are applied on the surface of a substrate in order to stimulate osteointegration. Laser cladding uses a high-density laser source which melts a feedstock material, usually in the form of wire or powder. The melted material may then be used to produce coatings. Industrial laser sources may reach high power density, so that the feedstock material may be melted in milliseconds without com-promising the properties of the substrate. Alternatively, the laser power may locally melt the surface of the substrate thereby allowing ceramic particles to be embedded into the substrate by the fluence of the laser. This allows for the use of laser cladding on "soft" substrates, such as polymers. For example, laser cladding may be used to deposit bioactive materials, such as silicon nitride, on soft low-melting polymers. Thanks to the high powder density of the laser source, the same technique can also be used to produce bioactive coatings. Cladded coatings can be used to improve osteointegration and prevent infections on substrates.

Silicon nitride has higher mechanical properties (hardness, toughness, resistance to cyclic loading, etc.) than conventional bioceramics and a series of additional bioactive effects which cannot be achieved with oxide-based materials. Silicon nitride may provide resistance to bacterial colonization, combined with the ability to stimulate osteoblast differentiation and production of bone tissue. Without being limited to any one theory, the beneficial effects of silicon nitride may be the result of the formation and release of both nitrogen ($NH_3$, $NH_4^+$) and silicon ($Si(OH)_4$) species. The nitrogen moieties stimulate cellular proliferation and lyse common bacteria strains; and silicon is converted to silicic acid which actively contributes to the formation of mineralized bone tissue.

Provided herein are biomedical implants or substrates with laser-cladded silicon nitride coatings, methods of coating the surface of a biomedical implant or substrate with silicon nitride using laser cladding, and methods of promoting osteogenesis using the biomedical implant with laser-cladded silicon nitride coating.

The method of coating the surface of a biomedical implant or substrate may include laser cladding a surface of a biomedical implant with silicon nitride powder. In some embodiments, the method may include providing the biomedical implant or substrate, roughening at least one surface of the biomedical implant or substrate, laser cladding a coating of silicon nitride on the roughened surface, and repeating the laser cladding step until the coating has a thickness of at least 10 μm. The laser cladding method may include directing a laser beam to the roughened surface of the biomedical implant or substrate and pre-applying a silicon nitride powder or simultaneously directing a silicon nitride powder to the roughened surface of the biomedical implant or substrate. In one example, laser cladding of silicon nitride on substrates may result in the formation of a composite coating based on silicon nitride particles in a matrix of titanium, and nanocrystalline and amorphous silicon.

Non-limiting examples of materials that may be included in the biomedical implant or substrate include polymers, titanium, titanium alloys, alumina, zirconia, mixtures of alumina and zirconia, stainless steel, and cobalt chromium alloys, polyethylene, polyurethane, polyetheretherketone (PEEK), and/or polyetherketoneketone (PEKK). In various examples, the biomedical implant or substrate may include zirconia-toughened alumina (ZTA), yttria-stabilized zirconia (Y-TZP), titanium (Ti6Al4V), or low- or high-density polyethylene (LDPE, HDPE). In some embodiments, the biomedical implant may be a dental implant, a prosthetic joint, a craniomaxillofacial implant, a bone screw, a bone plate, a bone anchor, an arthrodesis implant such as an intervertebral spinal spacer or a podiatry foot wedge. In at least one example, the biomedical implant may be a dental zirconia substrate. In another example, the biomedical implant may be a titanium prosthetic joint. In another example, the biomedical implant may be a polyetheretherketone spinal spacer. Laser cladding of silicon nitride powders on to zirconia, titanium, or polyetheretherketone substrates may result in the formation of a coarse layer of silicon nitride particles embedded in the ceramic, metal, or polymer substrate.

In an embodiment, the method may include roughening at least one surface of a biomedical implant or substrate. Without being limited to any one theory, roughening the surface may increase the ability of the silicon nitride particles to bond to the surface. The roughening may include abrading the surface of the substrate. In some examples, the substrate may be scratched in a linear pattern, a grid pattern, or at random. The scratches may be formed by diamond abrasive or a glass-cutter diamond blade. In one example, the blade may have a diameter of about 5 μm to about 500 μm. In some embodiments, roughening at least one surface of the biomedical implant may include forming a first set of unidirectional scratches on the at least one surface, rotating the biomedical implant by about 90°, and forming a second set of unidirectional scratches perpendicular to the first set of unidirectional scratches. The scratches may be about 5 μm to about 500 μm wide. In various examples, the scratches may be about 5 μm to about 50 μm, about 5 μm to about 10 μm, about 10 μm to about 20 μm, about 20 μm to about 30 μm, about 30 μm to about 40 μm, about 40 μm to about 50 μm wide, about 50 μm to about 100 μm wide, about 100 μm to about 200 μm wide, about 200 μm to about 300 μm wide, about 300 μm to about 400 μm wide, or about 400 μm to about 500 μm wide. In at least one example, the scratches may be about 25 μm wide. In other embodiments, roughening at least one surface of the biomedical implant may include using a free diamond abrasive or sandblasting by any machine known in the art that may be used to abrade surfaces. The free abrasive machining or sandblasting may be used to form random scratches that may be 5 to 30 μm wide.

In an embodiment, the silicon nitride powder may include α-$Si_3N_4$, β-$Si_3N_4$, β-SiYAlON, SiAlON, or SiYON. The silicon nitride powder used in the laser cladding process may be formed from a two-phase microstructure including acicular β-$Si_3N_4$ grains separated by a continuous SiYON grain-boundary phase. The silicon nitride powder may be mechanically ground to an average particle size of about 1 μm to 15 μm.

In an embodiment, the powder may then be applied to the roughened substrate surface using laser cladding. FIG. 1 is an exemplary laser cladding system 100 that may be used to apply a silicon nitride coating to a substrate via laser cladding. In some embodiments, the system 100 may include one or more stepper motors 102, a powder tank 104 operable to hold silicon nitride powder, a powder feeder 106, a laser source 108, and a platform 110 operable to hold one or more substrates 112 to be coated with the silicon nitride. The system 100 may be operable to move the platform 110 and/or the powder tank 104 and powder feeder 106 in the x, y, and/or z directions.

Laser cladding may include applying the silicon nitride powder to the surface before or simultaneously with the application of a laser to bond the silicon nitride to the substrate. The laser beam creates a molten pool at the substrate surface, to which the silicon nitride powder is added. The exposure time of the laser on the substrate may be short, such that the cooling is quick. The properties of the laser may be selected such that there is bonding of the silicon nitride powder to the substrate. For example, any combination of laser type, energy and power setting, voltage, pulse and spot size known in the art that achieves the bonding of the silicon nitride powder to the substrate surface may be used. In at least one example, the laser wavelength may be about 1064 nm, have a max pulse energy of about 70 joule, a peak power of about 17 kW, a voltage range of about 160-500 V, a pulse time of about 1-20 ms, and/or a spot size of about 250-2000 μm. In some embodiments, the laser cladding may further include supplying a constant flux of nitrogen gas at the surface of the implant to limit silicon nitride decomposition and oxidation.

The morphology and stoichiometry of the cladded layer may be a function of the applied power, the amount of which may be dependent on the nature and composition of the substrate material. Without being limited to any one theory, the higher the applied power, the higher the amount of silicon there may be in the laser-cladded silicon nitride coating (e.g. silicon-rich, nitrogen-deficient coating). In particular, the nitrogen content may be present in the laser-cladded coating in a range from about 42 at. % to about 70 at. %. In a silicon rich silicon nitride laser-cladded coating, the coating may have between about 42 at. % to about 56 at. % nitrogen. For example, a higher power may lead to a more abundant presence of nanocrystalline silicon in the laser-cladded silicon nitride coating. Silicon plays an important role in the bone formation; in fact silicon ions contribute to the calcification of new bone. For example, the increased silicon ions and the increased surface roughness in claddings on titanium may result in a more homogeneous distribution of cells and bone matrix.

As a non-limiting example, it has been fortuitously found that specific laser power settings and raster speeds lead to appropriate embedding of silicon nitride into titanium. Using a 100 Watt picosecond laser source specifically tuned to emit nanosecond pulses at a raster speed of 5,500 mm/s, it was discovered that one preferred power level and pulse width were 10% to 25% and 20 to 500 μm, respectively. A more preferred power level and pulse width were 15% to 25% and 20 to 500 μm, respectively; and a most preferred power level and pulse width were 25% and 200 to 500 μm, respectively. In addition to the power and pulse width settings, it was also fortuitously discovered that the laser pulse frequency, hatching distance, hatching overlap, and distance of impact all played important roles in obtaining a preferred silicon nitride coating. Hatching distance is the separation of the lines as they are put down (orthogonal to laser beam path) and distance of impact is the center-to-center separation of the individual pulse locations parallel to beam path. A preferred range for pulse frequency is from 110 to 1000 kHz, whereas a most preferred frequency is 1000 kHz. A preferred hatching distance ranges from 0.03 to 0.05 mm, whereas the most preferred hatching distance is 0.03 mm. The most preferred hatching overlap is 60.34%. The preferred distance of laser impact is 0.05 to 0.0055 mm whereas the most preferred distance is 0.0055 mm.

The application of the laser and powder may be repeated at least 1, at least 2, at least 3, at least 4, or up to 5 times in order to obtain a homogenous coating. In some examples, the laser-cladded coating of silicon nitride may have a thickness of at least 5 μm, at least 10 μm, at least 15 μm, at least 20 μm, at least 25 μm, or at least 30 μm. The coating may include about 5 wt. % to about 15 wt. % silicon nitride.

The cladding coating may be effective for osteointegration. The cladded layers may contribute to bone formation and may provide a variable degree of protection against gram-positive bacteria, in particular for Ti6Al4V substrates. In an embodiment, a method of promoting osteogenesis may include contacting the biomedical implant or substrate with a laser-cladded silicon nitride coating with human tissue. Without being limited to any one theory, the altered composition (sub-stoichiometric nitrogen content) and the crystallographic structure of the cladding may lead to a reduction of the cellular proliferation and surface colonization when compared to monolithic materials. Surprisingly, the silicon nitride cladding induced the formation of a significantly higher amount of bone tissue than the substrate without cladding, even if they had similar values of cell proliferation, and also had a higher surface colonization when observed with fluorescence microscopy.

In some embodiments, bone tissue production increases on the silicon nitride laser-cladded biomedical implant as compared to an implant without the laser-cladded silicon nitride coating. For example, the silicon nitride laser-cladded biomedical implant may have increased osteocalcin and osteopontin distributions, the bone tissue may have a higher degree of cross-linking, and/or may have increased mineralized tissue such as an increase in mineral hydroxyapatite on the surface of the implant. The laser-cladded coating contributes to the stimulation of bone tissue. For example, when compared to uncoated zirconia, silicon nitride cladding may provide improved cellular adhesion and bone tissue formation, with higher degrees of maturity and overall better quality parameters as measured by Raman spectroscopy. The flexibility of the laser cladding technology, based only on a $Si_3N_4$ powder feeder and a laser beam source, makes this technology suitable also for complex component designs.

EXAMPLES

Example 1: Silicon Nitride Laser Cladding of Yttria-Stabilized Zirconia Samples

Sample Production

Yttria-stabilized zirconia samples containing 3% of yttria were obtained from a commercial producer. Polished and powdered silicon nitride discs (12 mm diameter, 1 mm thickness) were provided by SINTX Corp. The material consisted of a two-phase microstructure including acicular $β-Si_3N_4$ grains separated by a continuous and sub-micrometer sized film of Si—Y—O—N grain-boundary phase. To obtain the ceramic powder, coarse powder was mechanically ground to an average particle size of 15 µm.

To produce a "roughening effect" on the otherwise smooth zirconia substrates, the surface was abraded using a glass-cutter diamond blade (tip diameter: 25 µm) under an applied load of 20±5 N. Once the surface was covered by unidirectional scratches, the scratching direction was rotated by about 90° and the operation was repeated.

A schematic of the overall laser-sintering procedure and system is presented in FIG. 1. The conditions applied to achieve a $Si_3N_4$-cladding were the following: laser wavelength 1064 nm, max pulse energy: 70 joule, peak power 17 kW, voltage range 400 V, pulse time 4 ms, and spot size 2 mm. The apparatus operated under a constant flux of nitrogen gas in order to limit $Si_3N_4$ decomposition and oxidation. The operation was repeated 3 times in order to obtain a homogenous coating with a thickness of 15±5 µm, over the entire surface of the substrate. A motorized x-y stage with a lateral precision of 10 µm was used to align the sample to the laser source.

Microscopy and Spectroscopy

Micrographs were taken using a 3D laser-scanning microscope with magnifications ranging from 10× to 150× and a numerical aperture between 0.30 and 0.95. The microscope used an automated x-y stage and an autofocus function for the z range, allowing the acquisition of composite images. The surface roughness values were obtained at 20× magnification, and an average of 10 measurements were performed on areas of 500×500 µm.

Figure 2:
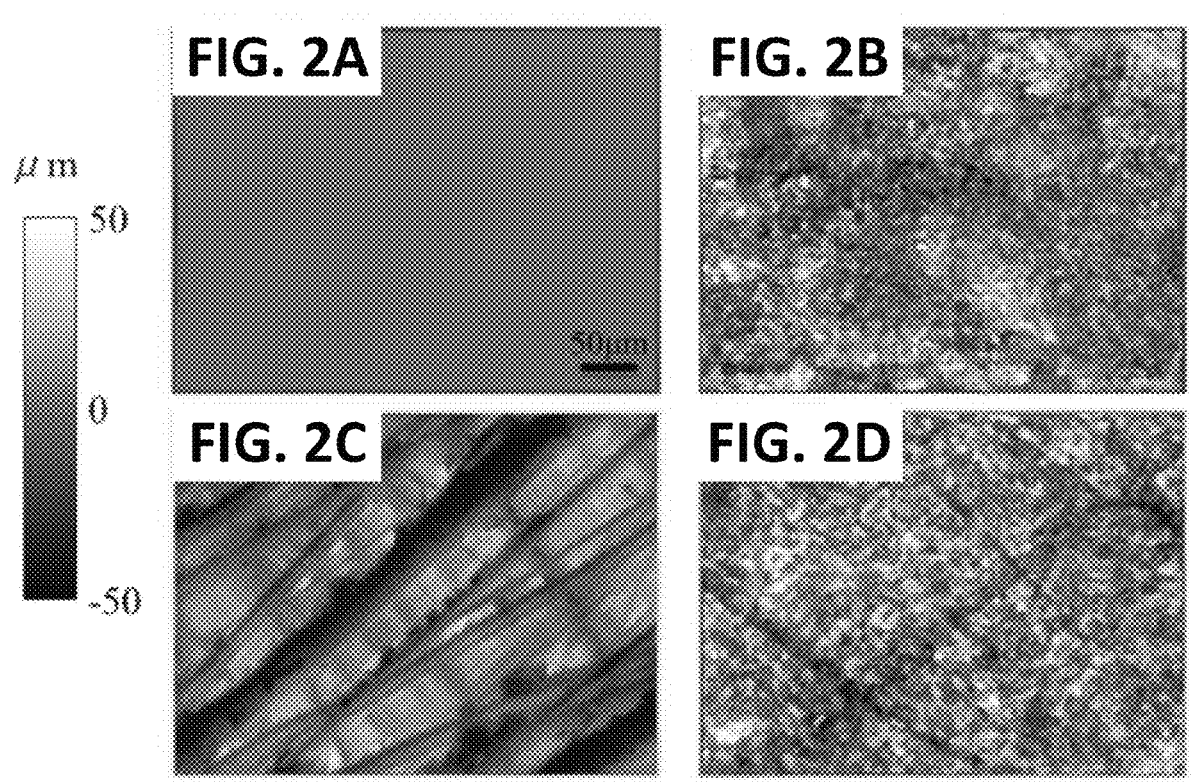
FIG. 2A shows the surface morphology of polished zirconia before laser cladding, obtained by laser microscopy.
FIG. 2B shows the surface morphology of polished zirconia after laser cladding, obtained by laser microscopy.
FIG. 2C shows the surface morphology of roughened zirconia before laser cladding, obtained by laser microscopy.
FIG. 2D shows the surface morphology of roughened zirconia after laser cladding, obtained by laser microscopy.

FIGS. 2A-2D shows the morphology of the surface of the pristine polished zirconia surface (FIG. 2A) compared to the roughened substrate (FIG. 2C) and the correspondent surfaces after the application of the $Si_3N_4$ laser-cladded coating (FIGS. 2B and 2D). The laser-cladding process produced a coarse surface where partially embedded $Si_3N_4$ powder particles are still clearly visible, resulting in the formation of two different orders of roughness: a "macroscopic" local variability of the coating thickness and a microscopic roughening due to the protrusion of powder particles. The roughening process resulted in the formation of oriented scars with a depth of up to about 50 µm that are clearly visible after the application of the coating (FIG. 2D).

Figure 3:
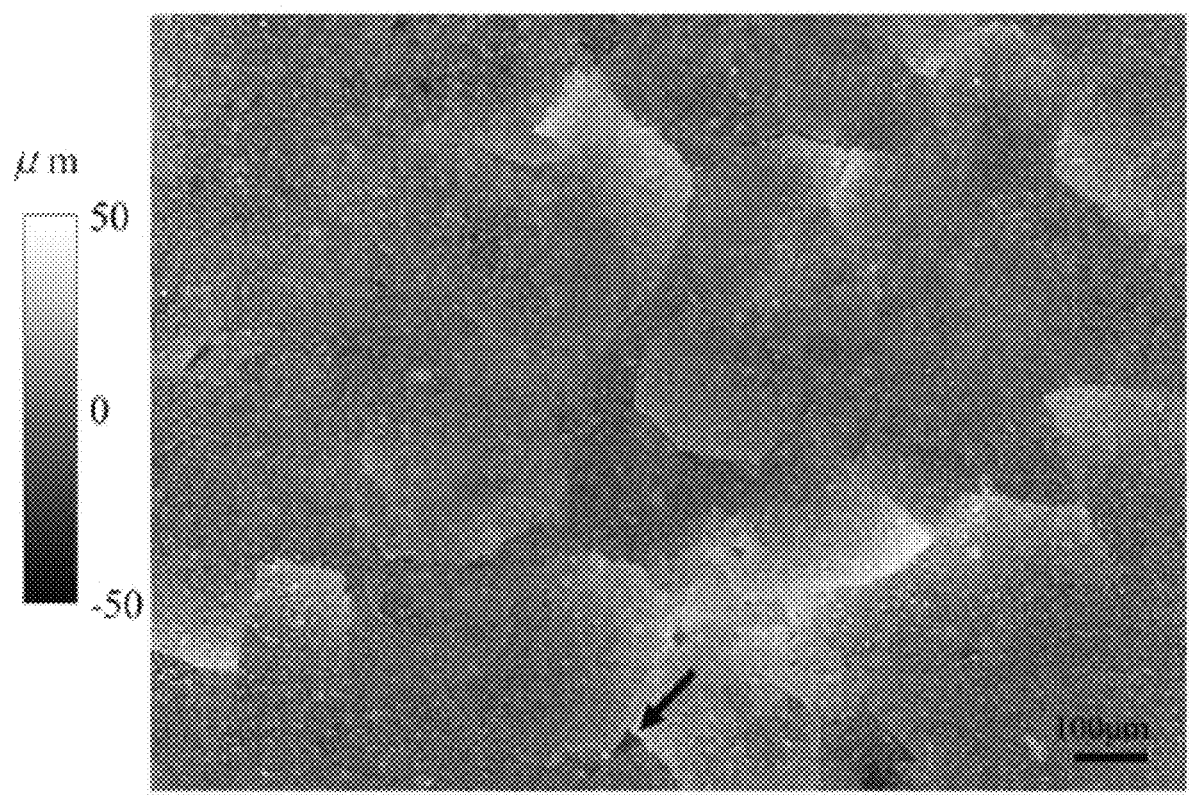
FIG. 3 shows surface morphology of a polished and laser-cladded zirconia sample with a net of buckling cracks clearly visible.

At lower magnifications, a network of cracks was observed on the coated polished zirconia samples (FIG. 3). The shape and topography of the cracks are likely associated with the presence of a buckling phenomenon caused by compressive stresses on the coating. It was observed that the cracks did not result in massive coating delamination, as only small portions of material were missing at the intersections of three or more ridge cracks (black arrow). Compressive residual stresses occurring during solidification are likely due to the difference in coefficient of thermal expansion for the various phases. The application of the roughening process ahead of cladding was helpful to reduce the stress concentration and improve coating adhesion, thereby preventing crack formation.

Figure 4:
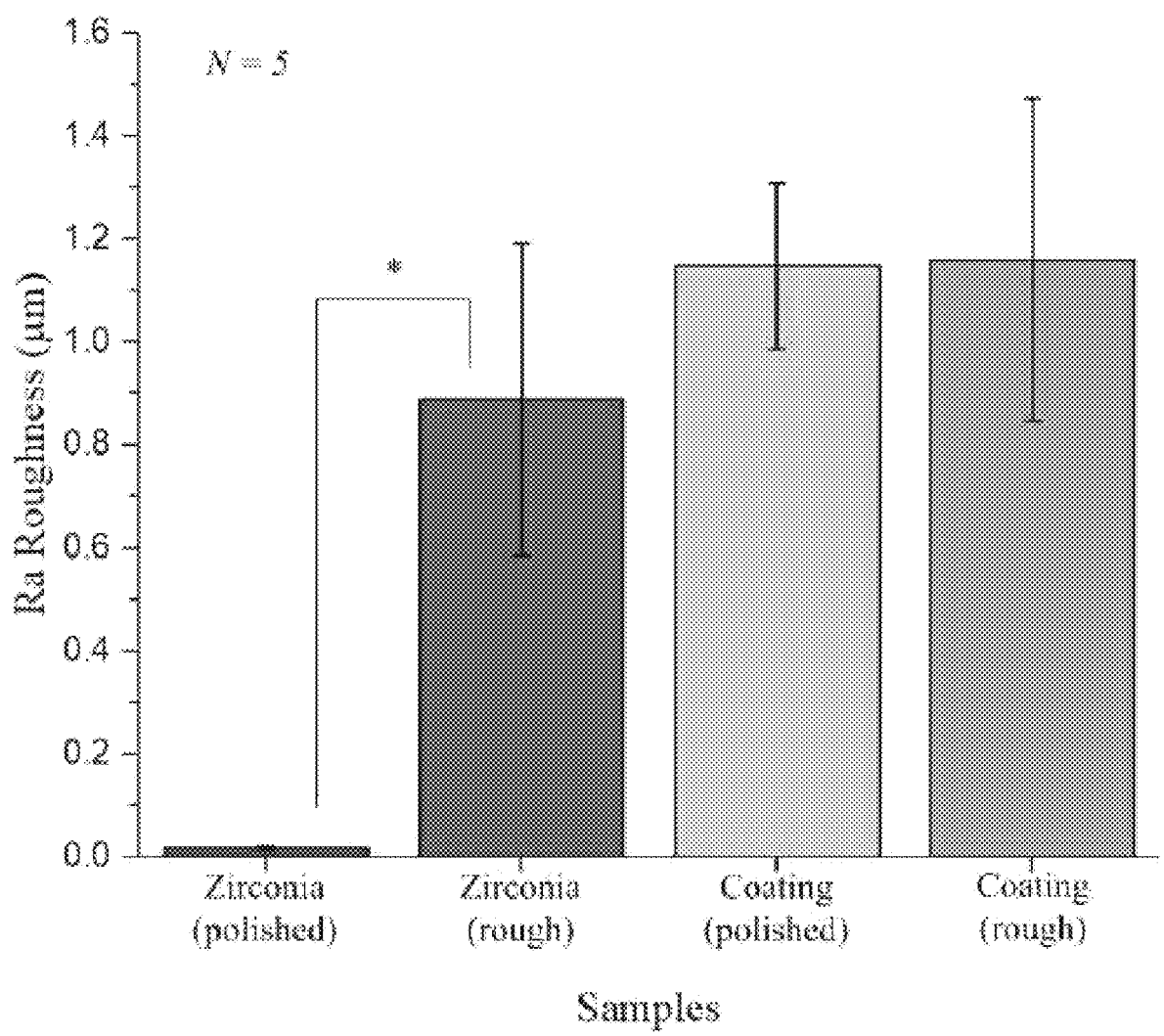
FIG. 4 shows surface roughness (Ra) of uncoated and coated zirconia, measured by laser microscopy.

FIG. 4 shows the surface roughness values measured on the different samples using a magnification of 50×. It was observed that the roughening process resulted in values comparable to those achieved after laser-cladding. There was no statistically relevant difference in the surface roughness for the laser-cladded coatings applied to either the polished or surface-roughened zirconia substrates.

A field-emission-gun scanning electron microscope was used to observe and characterize the surface of the samples, before and after cell culture. All images were collected at an acceleration voltage of 10 kV and magnifications ranging between 100× and 50,000×. All samples were sputter-coated with a thin (20 to 30 Å) layer of platinum to improve their electrical conductivity. Crystallographic analyses were performed using a scanning electron microscope (SEM) equipped with an electron-backscattered X-ray diffraction (EBSD) detector.

FIGS. 5A and 5B show the SEM images of the $Si_3N_4$ powders used for the cladding process. It was observed that the grains were sharp and polygonal, from about 300 nm up to a few µm. FIG. 5C shows an isometric view of the coating cross section, with a few, representative thickness values obtained using SEM software. The thickness distribution, from averaging 250 single measurements, is presented in FIG. 5D.

FIGS. 6A-6D show the surface of the roughened zirconia substrates before and after laser-cladding at different magnifications. In FIG. 6A the scratches have two main orientations with a difference of almost 90°. This was selected as the best condition to achieve uniform adhesion of the coating and avoid preferential orientation. At higher magnifications (FIG. 6B), it was observed that the roughening process resulted in the formation of small debris, the amount of which roughly correlated with the depth of the relative abrasion. For the coating, low magnification analysis (FIG. 6C) showed a generally good coverage of the substrate, with only localized defects that look like small cracks or intergranular voids. At higher magnifications (FIG. 6D), the coating revealed a composite structure with a dispersion of micron and sub-micron globular particles protruding from the surface and forming a classical "cauliflower morphology".

Raman spectra were collected at room temperature using a triple monochromator equipped with a charge-coupled device (CCD) detector. The spectra were analyzed by commercially available software. The excitation source in the present experiments used a 532 nm Nd:YVO4 diode-pumped solid-state laser operating with a nominal power of 200 mW. A confocal pinhole with an aperture-diameter of 100 µm was placed in the optical circuit to shallow the probe to the order of few µm in depth by excluding photons scattered from out-of-focus regions in the irradiated volume. The lateral resolution of the Raman micro-probe was on the order of 1 µm. An automated, two axes sample stage was employed, making it possible to record spectral maps at given depths by focusing above (or below) the sample surface, and to map spectra with high lateral resolution. For each sample, 25 randomized locations were investigated, and the resulting spectra averaged. All spectra were post-processed removing the baseline and reducing noise with a moving average filter. After fitting to Gaussian curves, the intensity of specific bands (at 1658 and 1691 $cm^{-1}$ for collagen, 1070 $cm^{-1}$ for carbonate apatite and 961 $cm^{-1}$ for phosphate apatite) were used to evaluate the collagen maturity, the phosphate/carbonate ratio and the mineral to matrix ratio.

Figure 7:
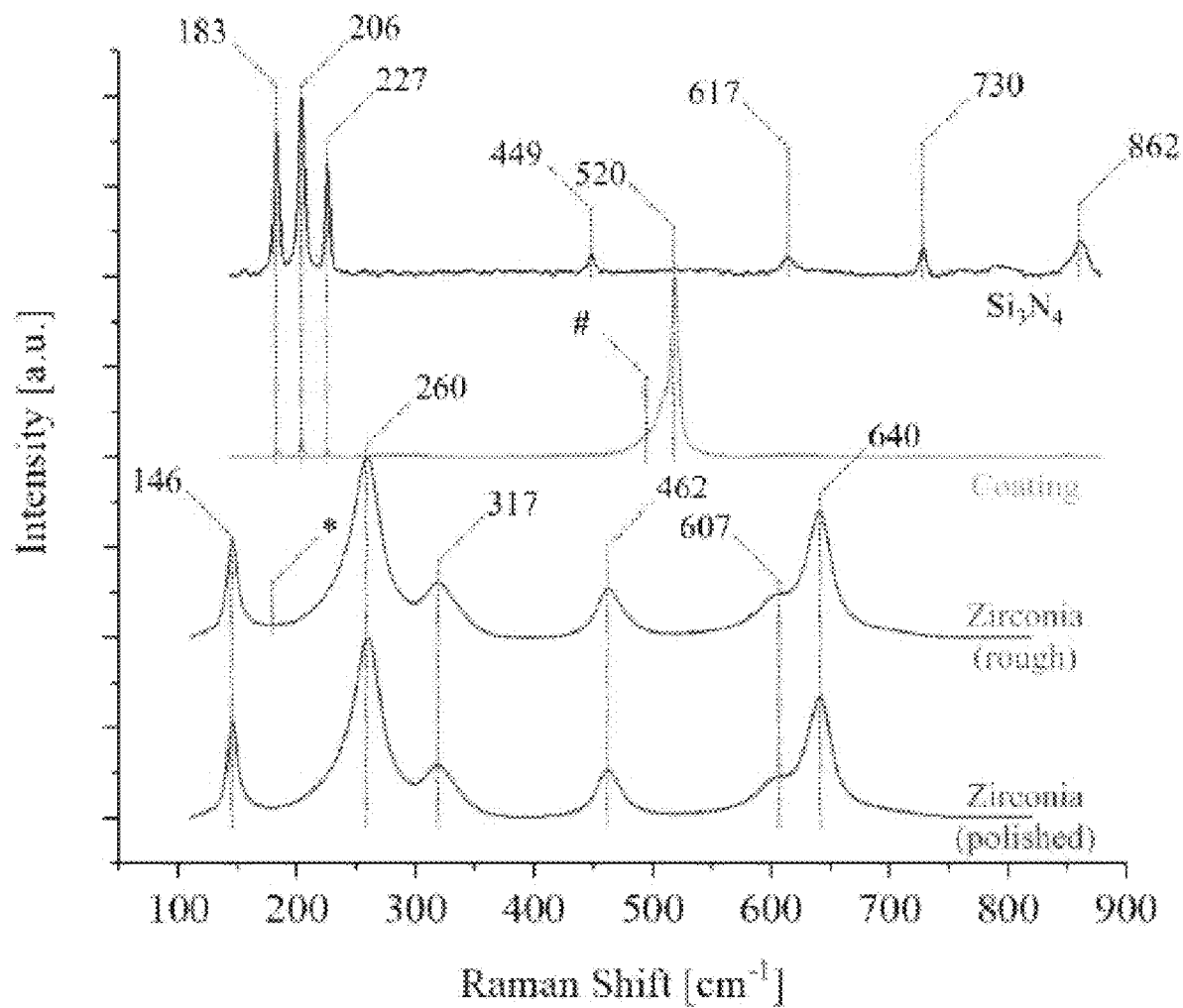
FIG. 7 shows Raman spectra of both zirconia substrates, the laser-cladded layer and stoichiometric $Si_3N_4$ as a reference.

The Raman spectra of the different samples are presented in FIG. 7. The polished substrates were found to be 100% tetragonal zirconia. After roughening, two small peaks related to monoclinic zirconia appeared at about 180 and 192 $cm^{-1}$ (marked with a "*"). The total amount of monoclinic zirconia was estimated by Raman Spectroscopy using the Katagiri equation. As expected, the value was 0% in the polished areas between scratches, but reached values up to 3% as a result of the diamond blade scratches. The average value on the whole surface was 0.55±0.22%.

The spectra of the coated samples were dominated by a strong band at about 520 $cm^{-1}$ which is associated to Si—Si vibrations. The asymmetry of the band (to lower Raman shifts) was caused by the presence of a region of sub-bands (marked as "#"), which resulted from nano-crystalline domains of silicon with varying average diameters trapped inside the amorphous silicon matrix. Due to their smaller Raman cross-section, residual Si—N bonds were only observed in the three bands in the region between 150 and 250 $cm^{-1}$, as confirmed by a comparison with the reference spectrum of stoichiometric $\beta$-$Si_3N_4$.

Analysis of the composition of the laser-cladded silicon nitride layer on the zirconia by Raman spectroscopy showed the presence of a series of sub-bands close to the peak related to Si—Si bonds at 520 $cm^{-1}$. Even if these sub-bands indicate the presence of sub-micron grains, Raman scattering alone could provide unambiguous information regarding the crystallite size, fraction and distribution. Additional investigations performed using electron backscattered X-ray diffraction were also not able to resolve the crystal structure of the matrix of the laser-cladded layer either, supporting the amorphous/nano-crystalline hypothesis.

Figure 8A:
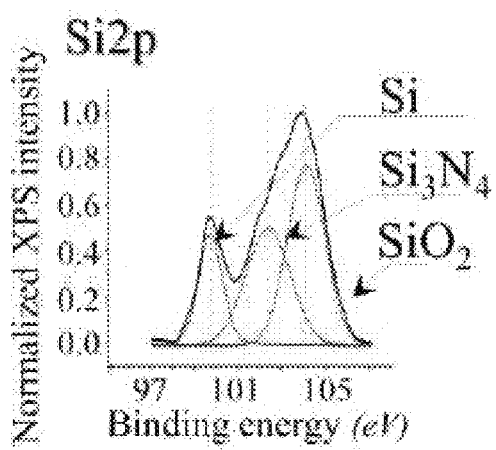
FIG. 8A shows a composition of the laser-cladded surface obtained in the region of Si2p.
Figure 8B:
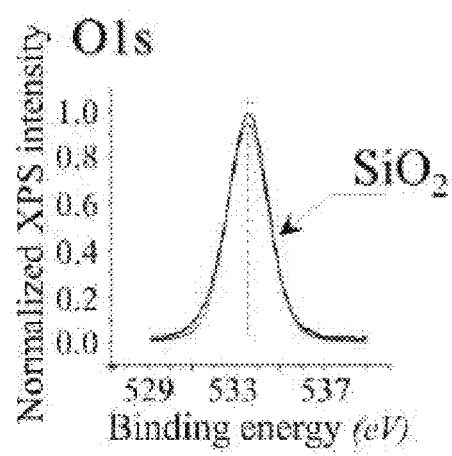
FIG. 8B shows a composition of the laser-cladded surface obtained in the region of O1s.
Figure 8C:
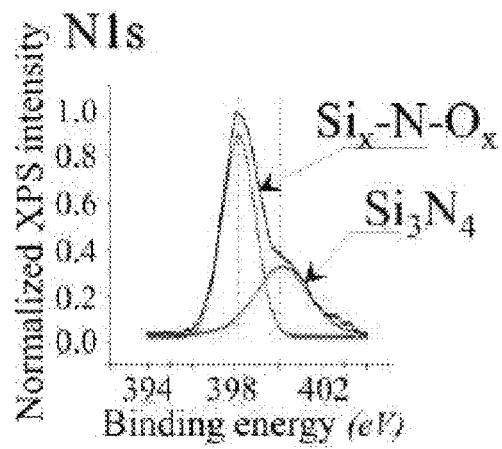
FIG. 8C shows a composition of the laser-cladded surface obtained in the region of N1s.
Figure 8D:
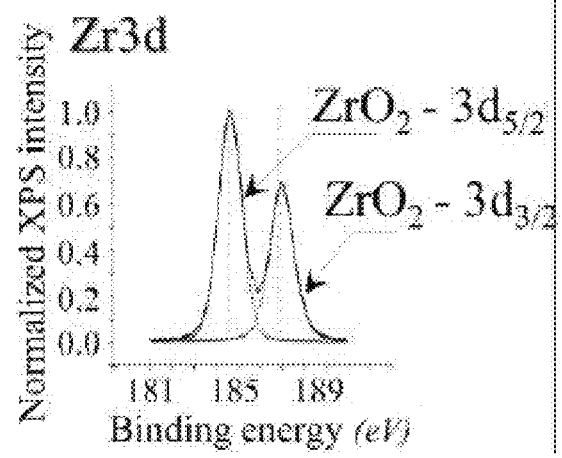
FIG. 8D shows a composition of the laser-cladded surface obtained in the region of Zr3d.
Figure 8E:
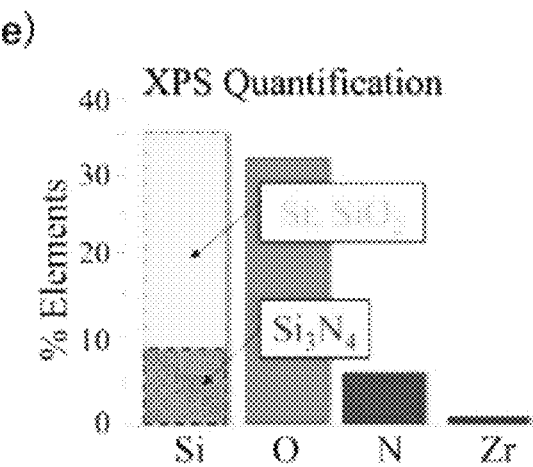
FIG. 8E is a quantification of FIGS. 8A-8D.

FIGS. 8A-8D shows the XPS spectra of silicon, oxygen, nitrogen and zirconium measured on the coated samples. FIG. 8E is a quantification of FIGS. 8A-8D. The signal of silicon was de-convoluted in three main bands: metallic silicon (100 eV), silicon nitride (102.5 eV) and silicon oxide (104 eV). It was observed that silicon nitride accounts for only about 28% of the silicon content, silicon oxide being the strongest signal, as also confirmed by the spectrum at about 533.5 eV and related to oxygen (1 s) bonds. As the deposition was performed under a constant nitrogen flux, the possible initial sources of oxygen were limited to gas trapped in the powders or chemically bound to the silicon nitride in the form of silicon oxide or silicon oxynitride. After deposition, the outermost layer of metallic silicon (Si—Si) spontaneously reacted with the humid atmosphere, resulting in the formation of a thin, uniform layer of silicon oxide. The presence of silicon-nitrogen-oxygen bonds was also confirmed by the spectra of nitrogen (1 s) at about 400 eV. Two main peaks were observed: stoichiometric silicon nitride (400 eV) and Six-N-Ox phases, resulting from partial oxidation (398 eV). Finally, all zirconium ions detected by XPS (185-187 eV) appeared to be bonded with oxygen, meaning that the only possible source for such a signal was the residual exposed substrate.

XPS analysis gave further insight to the composition and chemical structure of the layer. As it was observed, only a fraction of the silicon was bonded to nitrogen atoms. Most of it was oxidized, probably due to the exposure to the environment during deposition. An intermediate phase of silicon oxynitride was observed at around 398 eV (N1 s). These findings support the bonding structure of silicon oxynitride prepared by oxidation of Si-rich silicon nitride and the spontaneous formation of mixed nitrides/oxides phases when exposed to an oxidizing environment.

X-ray Diffraction (XRD) analysis were performed using a benchtop MiniFlex 300/600 diffractometer equipped with a Cu source, in a 2θ/θ configuration. The 2θ range was comprised between 10 and 90° with a step of 0.01°.

Figure 9:
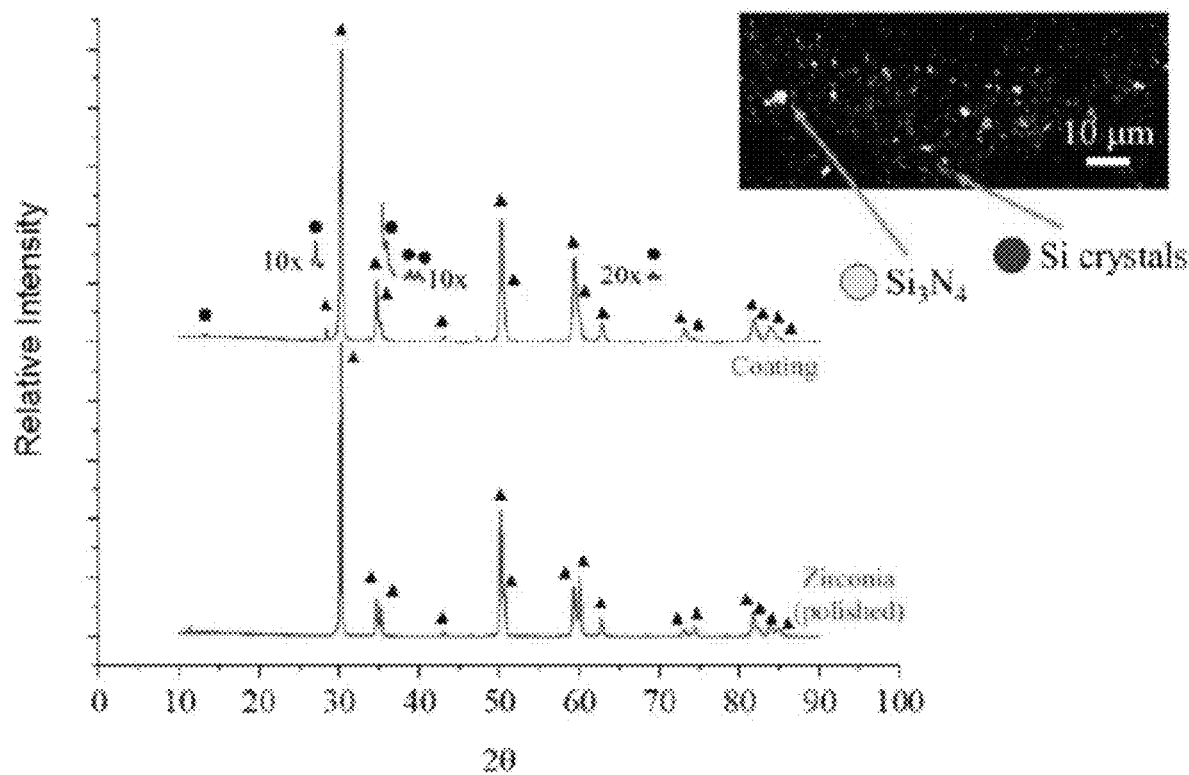
FIG. 9 shows XRD crystallographic patterns obtained on polished zirconia and on the laser-cladded coating. The inset shows an EBSD image of the cross-section of the coating with $Si_3N_4$ (yellow) and crystalline Si—Si domains (red) clearly visible.

The XRD patterns of the zirconia substrate and coated sample are presented in FIG. 9. The zirconia was observed to be the pure tetragonal phase. When the coating was applied, the overall morphology of the diffraction pattern was essentially unaltered, with a variation in the relative intensity of the two peaks at about 35°, at 60° and again at 84°, which indicated a preferential orientation of the grains. When the diffraction pattern was intensified by a factor 10× or by a factor 20×, secondary bands related to $\beta$-$Si_3N_4$ appeared. No other contribution from the coating was observed in FIG. 9, suggesting that the layer is actually mostly amorphous or nano-crystalline silicon. The results of a cross-sectional analysis performed by EBSD (inset) confirmed the presence of micron and sub-micron crystals of $Si_3N_4$ (yellow) dispersed in the matrix, further supporting the hypothesis that the coating was mostly formed by an amorphous or nano-crystalline phase.

Biological Testing and Assays

SaOS-2 human osteosarcoma cells were cultured and incubated in 4.5 g/L glucose DMEM supplemented with 10% fetal bovine serum. The cells were then proliferated in petri dishes for 24 h at 37° C. After adjusting the final cell concentration at 5×10$^5$ cell/ml, the cultured cells were deposited on the surface of $Si_3N_4$-coated and uncoated ZTA substrates (n=3 each) previously sterilized by exposure to UV light. Osteoconductivity tests were conducted by seeding the cells in an osteogenic medium (DMEM supplemented with 50 µg/mL ascorbic acid, 10 mM β-glycerol phosphate, 100 mM hydrocortisone, and ~10% fetal bovine calf serum), and then incubating the samples for 7 days at 37° C. The medium was changed twice during the week of incubation.

To observe and compare the substrates cytotoxicity, the samples were analyzed using a colorimetric assay based on water-soluble tetrazolium. This technique is based on the employment of a colorimetric indicator (WST-8) which produced a water-soluble formazan dye. The amount of the formazan dye generated was directly proportional to the number of living micro-organisms. Solutions were analyzed using micro-plate readers after collecting OD values for living cells.

Figure 10:
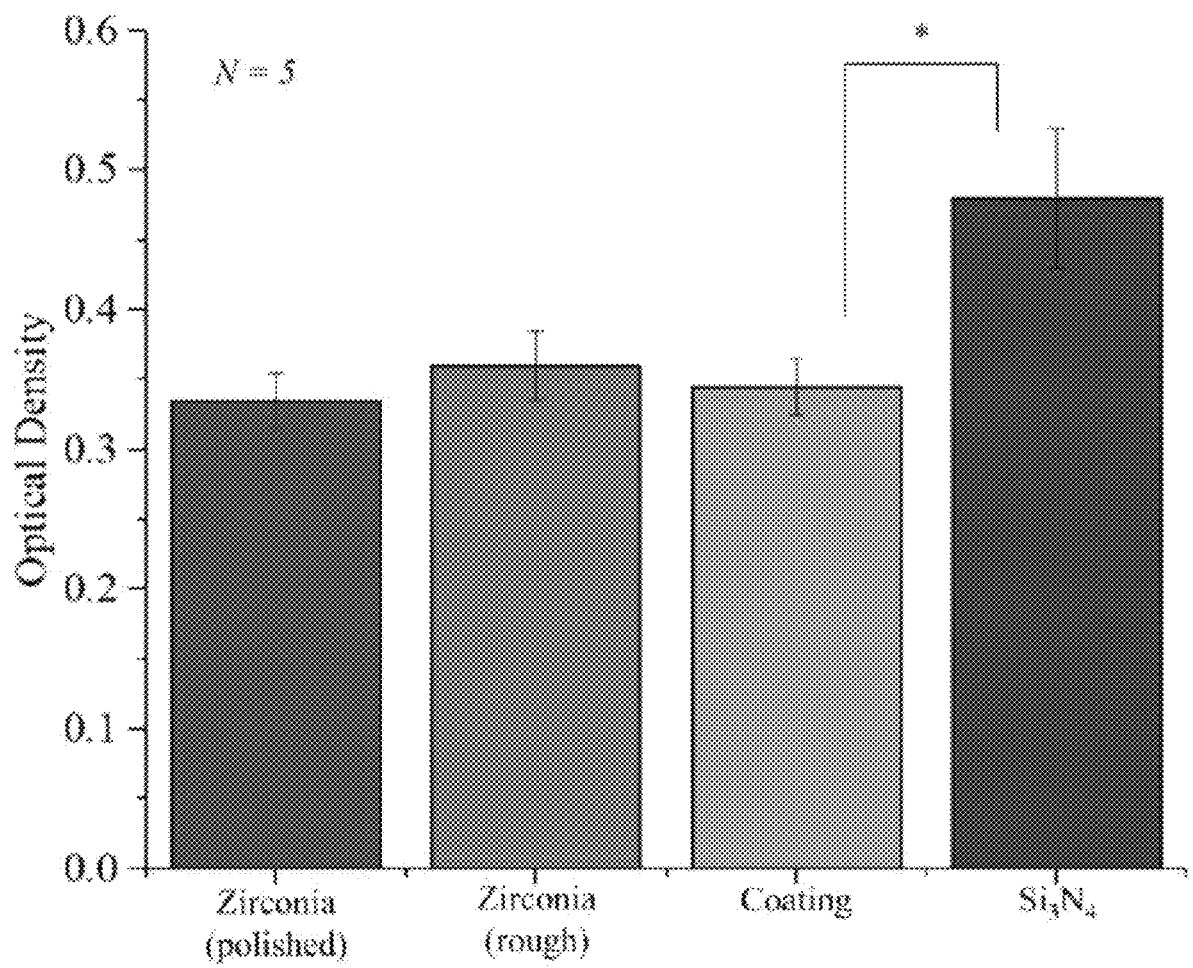
FIG. 10 shows WST optical density results measured after 10 days on the different samples and $Si_3N_4$ as a reference.

FIG. 10 shows the results of the viability tests performed with the use of a WST-8 assay. It was observed that the amount of cells on the zirconia samples and the laser-cladded surface after 10 days of exposure were similar. However, the optical density measured on the silicon nitride reference sample was significantly higher, meaning that more cells had colonized its surface. The different cellular response to the laser-cladded coating when compared to stoichiometric $Si_3N_4$ is due to different amounts of available nitrogen on the surface.

Because the structure of the laser-cladded layer is completely different from the base feedstock material, the cellular response of SaOS-2 osteosarcoma deviates from what was previously observed for stoichiometric or nitrogen annealed silicon nitride. Biological assay testing performed using water-soluble tetrazolium showed that while stoichiometric silicon nitride efficiently stimulates cell proliferation, laser cladding is comparable to bioinert materials such as zirconia.

After exposure to osteoblasts, each batch of samples was observed using fluorescence microscopy. Prior to examination, the sample surfaces were treated with different immunostaining reagents, including Hoechst 33342, anti-Human Osteocalcin Clone 2H9F11F8, Isotype IgG, Rabbit polyclonal antibody. Hoechst 33342, a cell nucleus stain, served to visualize cell proliferation, while the other two antibodies were used to stain matrix proteins osteocalcin and osteopontin, respectively, whose concentration quantifies the process of mineralization and bone matrix formation. Subsequently, a secondary antibody, Goat anti-Mouse IgG1 Antibody FITC Conjugated was added to enhance signal detection and visualization. Images were collected using 4× magnification and subsequently analyzed by imaging software in order to count the pixels related to the presence of the different stains.

Figure 11:
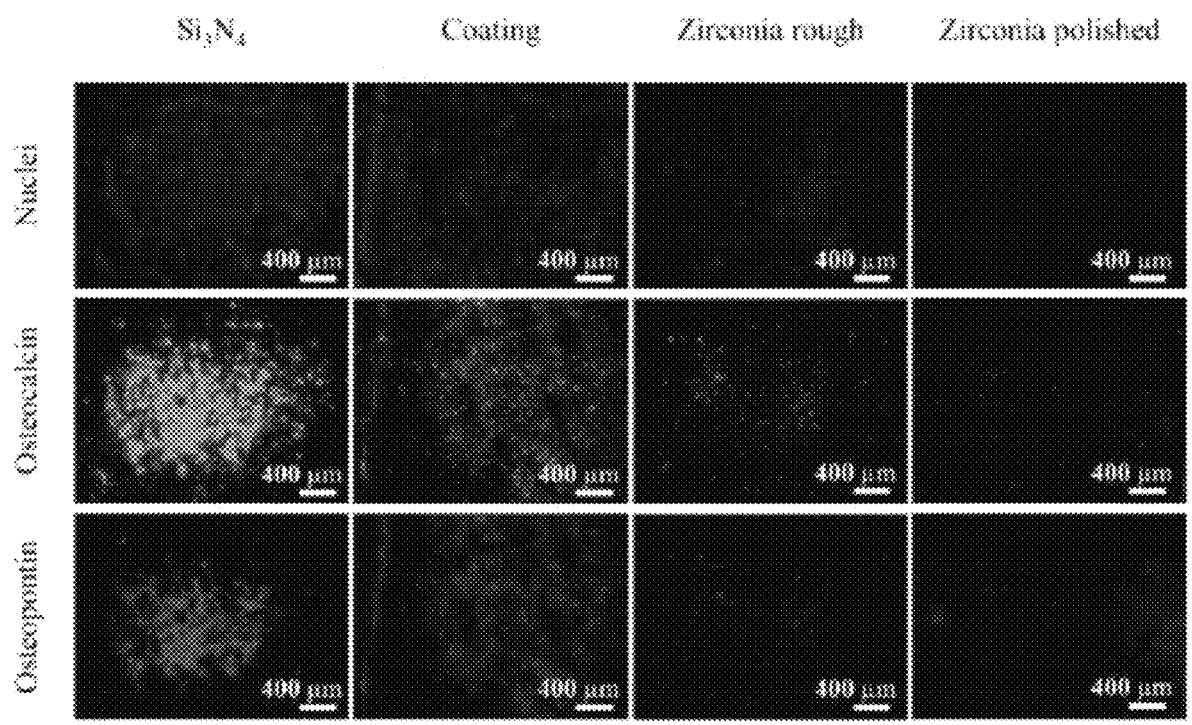
FIG. 11 shows fluorescence microscopy results obtained on the four different samples, showing the presence and distribution of cell nuclei (blue), osteocalcin (green) and osteopontin (red) on the surfaces.
Figure 12:
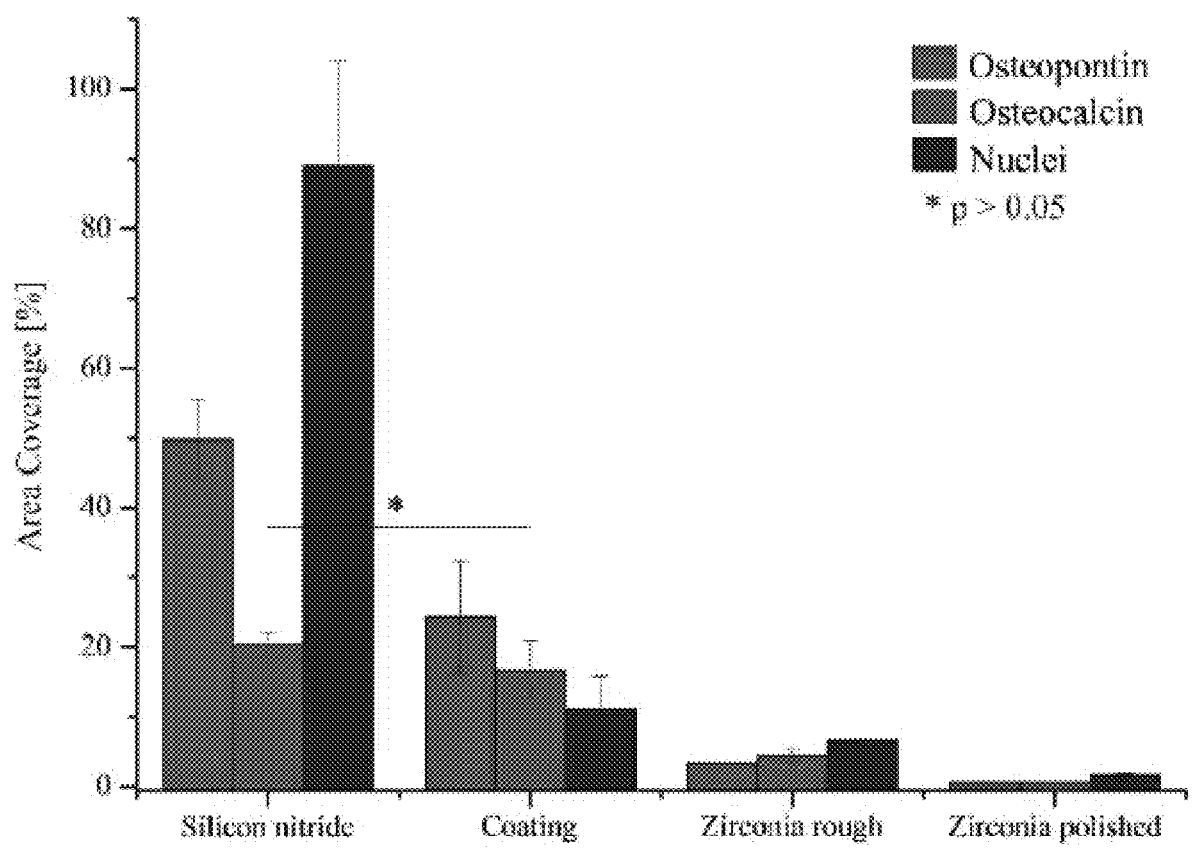
FIG. 12 shows results of SaOS-2 cell proliferation and bone formation test based on direct cell nuclei (blue), osteopontin (red) and osteocalcin (green) counting of fluorescence-stained microscopic images.

FIG. 11 shows the results of fluorescence microscopy on samples treated for 10 days with SaOS-2 osteosarcoma cells. Stoichiometric silicon nitride was used as a positive control. It was observed that the proliferation of cells on silicon nitride was higher than on zirconia. Roughened samples also generally showed a higher cellular adhesion when compared to smooth surfaces, but the coated zirconia was the only sample able to show a homogeneous distribution of cell nuclei across the entire surface. Moreover, both osteocalcin and osteopontin levels were greater on the coated samples, both smooth and rough zirconia. When compared to stoichiometric silicon nitride, the coated samples showed lower cellular proliferation and, consequentially, lower signals from osteocalcin and osteopontin. The area coverage ratios related to staining were measured and reported in FIG. 12. The results confirmed that the silicon nitride positive control presented the highest amount of cells with the highest synthesis of matrix proteins. The smooth zirconia samples showed the lowest ratios related to mineralized matrix formation.

The fluorescence microscopy images showed increased production of bone tissue for the laser-cladded surface when compared to the pure zirconia samples, as evidenced by both osteocalcin and osteopontin distributions. It must be noted that while both proteins are associated with the presence of bone tissue and their effects is considered synergetic, osteocalcin is mainly observed in mineralized tissue while osteopontin is often associated with bone remodeling. For both, the amount of fluorescence is intermediate between the rough zirconia and the reference silicon nitride sample. These results can be explained by the high bioavailability of silicon from amorphous and nanocrystalline sources when compared to macroscopic crystals.

Figure 13:
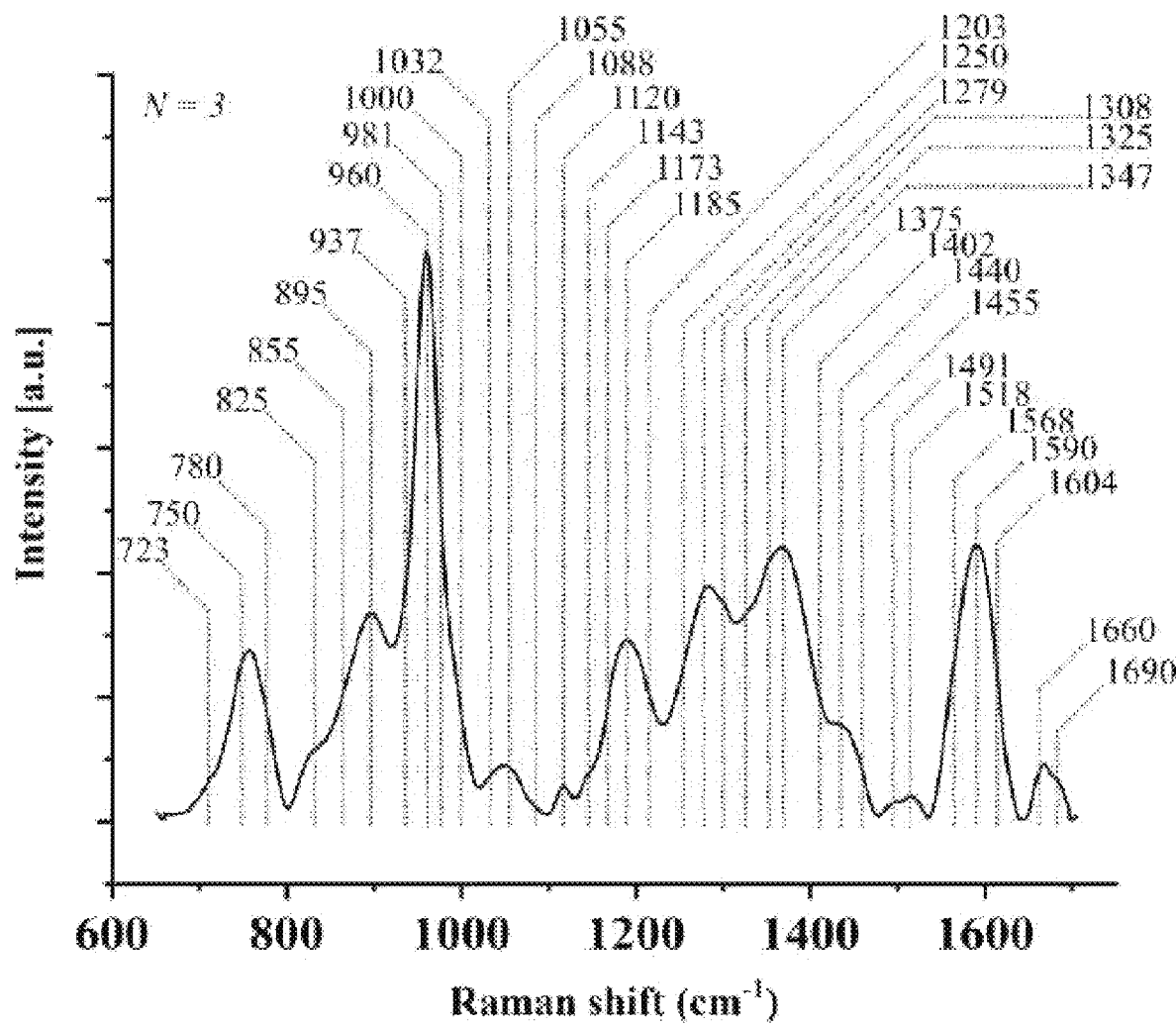
FIG. 13 shows reference Raman spectra of a laser-cladded surface after SAOS-2 testing for 10 days.

FIG. 13 shows a representative Raman spectrum acquired on the surface of the laser-cladded rough zirconia samples after SaOS-2 osteosarcoma testing in the region between 600 and 1800 $cm^{-1}$. The region can be roughly divided in four areas. The first region, between 600 and 1000 $cm^{-1}$, is dominated by a strong peak related to phosphate vibrations, at about 960 $cm^{-1}$. The second region, between 1200 and 1400 $cm^{-1}$ is associated with Amide III vibrations. The low-intensity bands in the region between 1400 and 1650 $cm^{-1}$ are assigned to fatty acids, while the stronger band at 1590 $cm^{-1}$ is associated with Amide II. Finally, the two relatively weak peaks at 1660 and 1690 $cm^{-1}$ are the results of Amide I vibrations.

Even if qualitative, the quality parameters obtained by Raman spectroscopy on the bone tissue formed on the laser-cladded layer are comparable to healthy bone and indicate a good degree of maturity, as shown by the values of crosslinking achieved in the bone collagen matrix.

Figure 14:
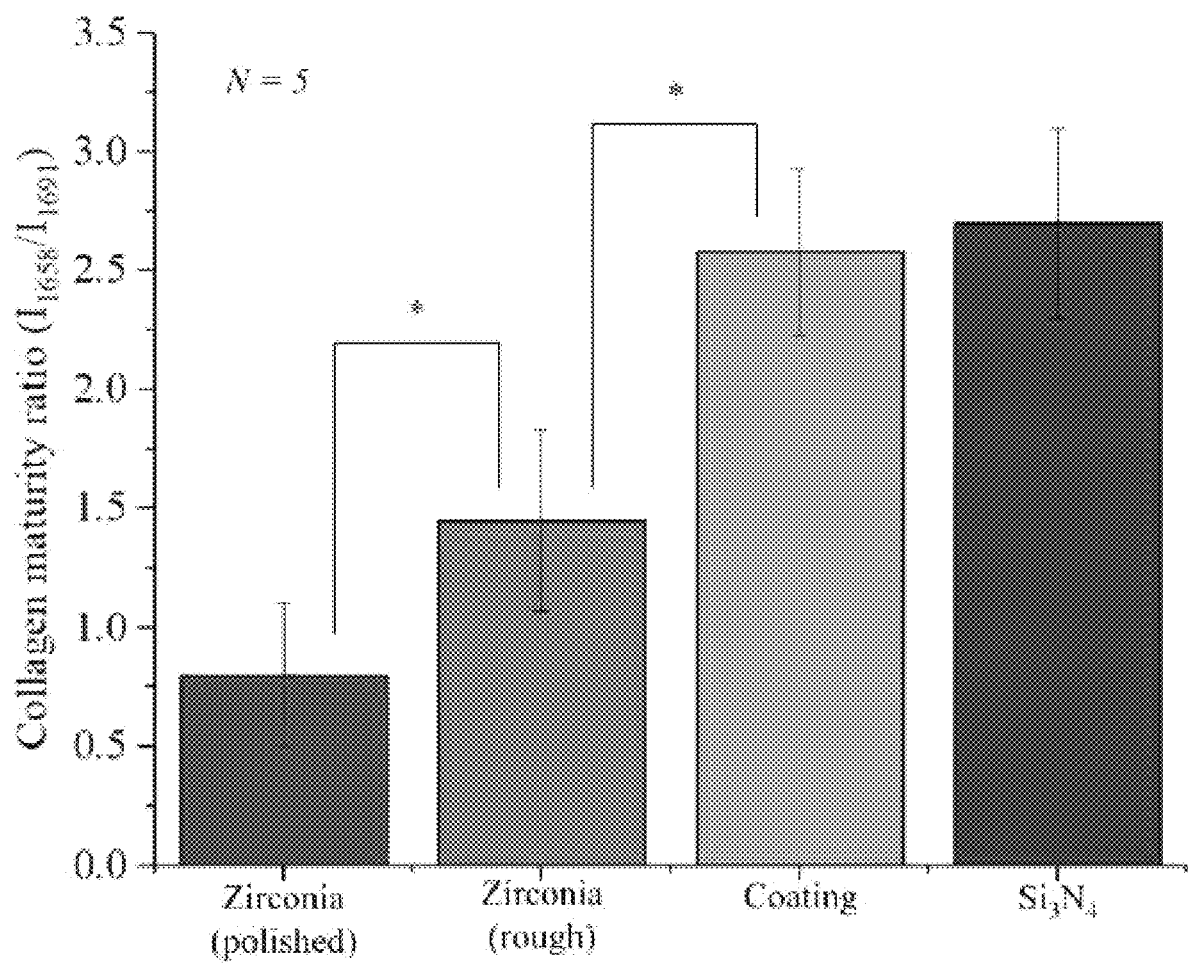
FIG. 14 shows collagen maturity ratio for the various samples obtained from the intensity of the Raman bands at 1658 and 1691 $cm^{-1}$.

FIG. 14 shows the Collagen Maturity Ratio for the four samples, based on comparing the intensities of the bands at about 1660 and 1690 $cm^{-1}$. It was observed that the collagen maturity ratio of the bone tissue developed by the osteosarcoma cells on both smooth and rough zirconia was relatively small, representing a low level of cross-linking and a high amount of reducible collagen. Tissue grown on silicon nitride and laser-cladded samples had a higher degree of cross-linking, which is associated with faster osteogenic development.

Figure 15:
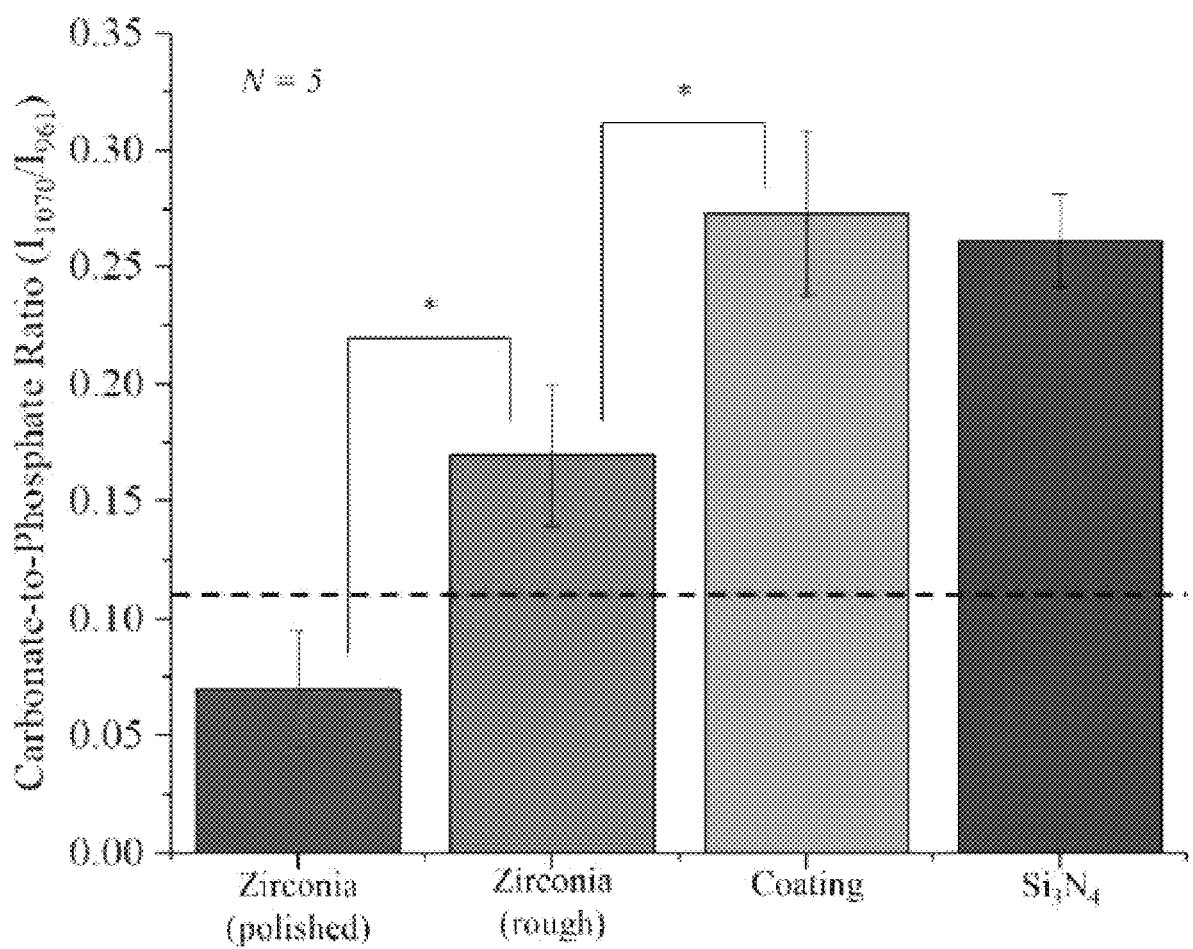
FIG. 15 shows carbonate-to-phosphate ratio for the various samples obtained by the intensity of the Raman bands at 1078 and 961 $cm^{-1}$.

FIG. 15 shows an estimation of the bone mineral phase quality, expressed as a ratio between the main peak related to carbonates and the peak related to phosphate vibrations, respectively at about 1078 and 960 $cm^{-1}$. It was observed that the amount of carbonate hydroxyapatite formed on the zirconia substrates was lower than on stoichiometric silicon nitride and the laser-cladded coating. Results for the polished zirconia substrate, in particular, were outside the ideal range of carbonate to phosphate percentage values (7-9% wt.) while the roughened zirconia barely reached the minimum value.

Figure 16:
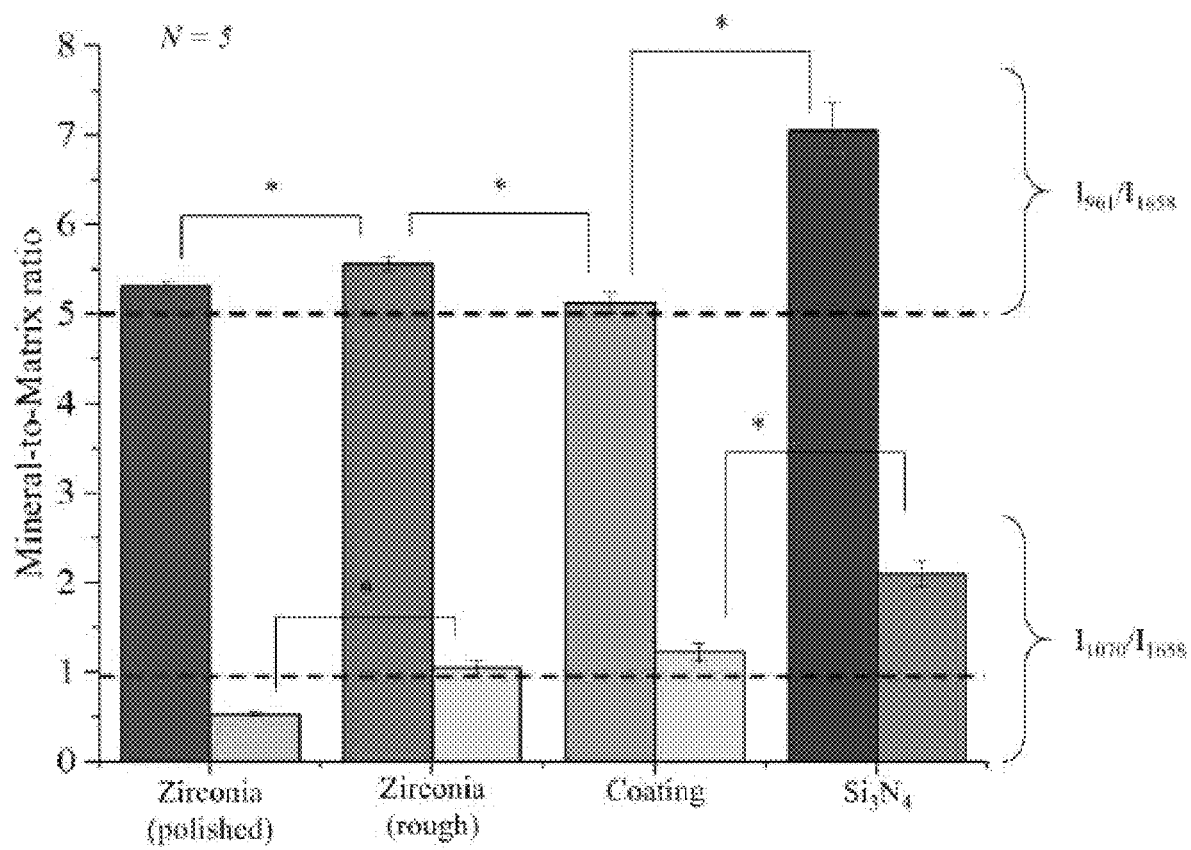
FIG. 16 shows mineral-to-matrix ratio for the various samples obtained by the intensity of the Raman bands at 961 and 1658 $cm^{-1}$ and at 1078 and 1658 $cm^{-1}$.

FIG. 16 shows the Mineral to Matrix ratio as estimated by the ratios between phosphate ion vibrations and carbonate ion vibrations with respect to the irreducible collagen at about 1660 $cm^{-1}$. The minimum value for both ratios is marked with a black dotted line. Three of the four tested specimens meet both requirements, the only exception being the polished zirconia surface, for which the carbonate over irreducible collagen ratio was under the minimum value. The best scores were obtained for the silicon nitride reference, which showed ratios well above the threshold values. Roughened and laser-cladded zirconia showed intermediate values and barely met both requisites, roughened zirconia having more intense phosphate bands and laser-cladded more carbonates.

Example 2: Silicon Nitride Laser Cladding of LDPE, Ti6Al4V, ZTA, and Y-TZP

Sample Production

In this example, $Si_3N_4$ bulk samples were used as a positive control for biological testing, and were prepared following a procedure previously described. Silicon nitride powder (which had a trimodal distribution with an average size of 0.8±1.0 μm) was obtained from SINTX Technologies Corporation.

Low-density polyethylene (Mw ~35,000) powder was melted in a vacuum oven at a pressure of 10 Pa and a temperature of 150° C. and molded into 30×50×5 mm plates. The plates were then cut into 10×10×5 mm samples and polished to a roughness of about 500 nm Ra.

Annealed medical grade Ti6Al4V (Al 6%, V 4%, C<0.10%, O<0.20%, N<0.05%, Fe<0.3%) rods with a diameter of 25 mm were cut into 5 mm-thick discs and polished to a roughness of about 500 nm Ra.

Zirconia-toughened alumina (ZTA) samples were obtained by slicing 40 mm diameter CeramTec Biolox®delta femoral heads to obtain 10×10×5 mm block. The cutting was performed with a 2 mm diamond coated blade rotated at 0.5 mm/min to minimize monoclinic zirconia transformation during the procedure. The femoral heads, produced in 2016, had a monoclinic zirconia volume fraction of about 6% before cutting.

Yttria-stabilized zirconia (Y-TZP) samples were obtained from fully densified 3Y-TZP bars (9×4×3 mm) containing 3 mol % of yttria ($Y_2O_3$) and 0.25 wt. % alumina ($Al_2O_3$). These samples were fabricated from raw powders using a hot isostatic pressing cycle (for 1 h at 1350° C.) following pressure-less sintering (at 1350° C.), and possessed an average grain size of about 0.2 μm.

A Vision LWI VERGO-Workstation Nd:YAG laser (wavelength of 1064 nm, max pulse energy: 70 joule, peak power 17 kW, voltage range 160-500 V, pulse time 1-20 ms, spot size 250-2000 μm) with an automatic x-y stage (lateral resolution: 10 m) was used to produce a silicon nitride coating. To achieve homogeneous coatings on the various substrate materials, the laser source parameters and the number of layers were adjusted through trial and error before each treatment. The pulse time was optimized to reduce surface overheating (and microstructural changes in titanium) or burning, while the voltage was selected as the lowest value that could grant at least a coverage of about 33% of the surface on the first cladded layer. The optimized parameters are listed in Table 1.

TABLE 1

Deposition parameters for various substrates. LDPE, low-density polyethylene; Ti6Al4V, titanium; ZTA, zirconia-toughened alumina; Y-ZTP, yttria-stabilized zirconia.

| Substrate | Voltage (V) | Pulse Time (ms) | Laser Spot Size (mm) | Layers | Gas |
|---|---|---|---|---|---|
| LDPE | 225 | 10 | 2 | 1 | $N_2$ |
| Ti6Al4V | 425 | 10 | 2 | 3 | $N_2$ |
| ZTA | 325 | 10 | 2 | 3 | $N_2$ |
| Y-TZP | 250 | 10 | 2 | 3 | $N_2$ |

A layer of silicon nitride powder of about 50 μm thickness was pre-coated on the surface of the samples and then heated with a 2 mm laser spot size under constant $N_2$ gas flow (1.5 atm). To cover all the surface substrate, the stage moved on the x-y stage with a step of 1 mm, in order to overlap the single laser spots and create a more homogeneous layer.

For the ZTA, the Y-TZP, and the Ti6Al4V, three cladding layers were required to achieve full coverage. Before depositing the next layer, the substrate was rotated by 90° to form a cross grid. However, only one layer was applied to the LDPE substrate because the laser easily melts and oxidizes polyethylene. Attempts at a second layer resulted in polymer carbonization.

Sample Characterization

Raman spectra and Raman maps were collected at room temperature using a RAMANtouch instrument with an excitation frequency of 532 nm green line and equipped with a 400 1340-pixel charge coupled device (CCD) camera. All data were analyzed using commercially available software (Raman Viewer, Laser RAMAN Microscope).

Surface morphology was characterized using a confocal scanning laser microscope capable of high-resolution optical imaging with depth selectivity. All images were collected at 50× magnification. The roughness of each sample was measured at 25 random locations.

Scanning electron microscopy (SEM) and energy dispersive X-ray spectroscopy (EDS) were used to acquire high magnification images and sample chemical composition maps.

Surface roughness plays a fundamental role in antibacterial properties and for this reason, the surface morphologies were studied and compared before and after deposition.

Figure 17A:
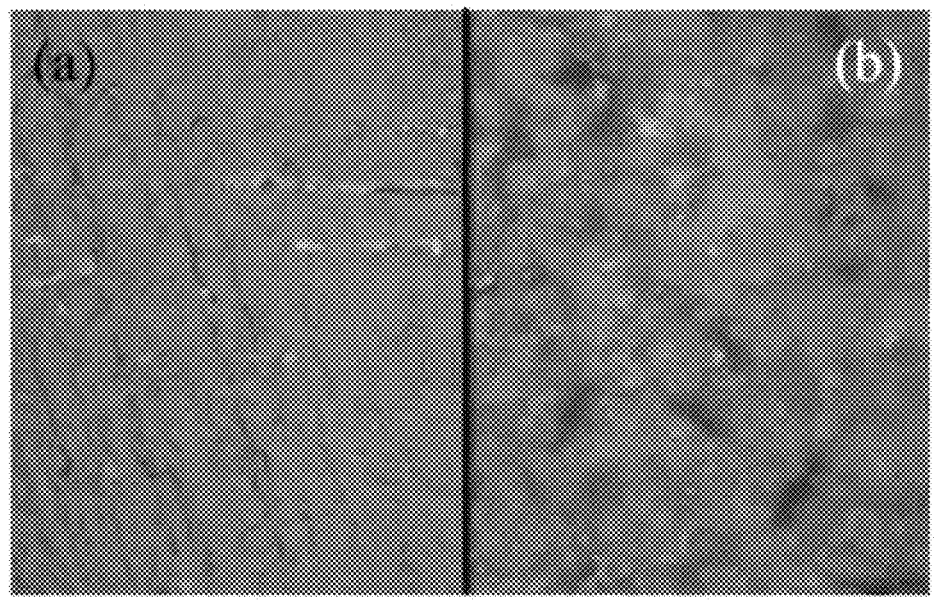
FIG. 17A shows a laser microscope substrate surface image of untreated LDPE.
Figures 17C, 17D:
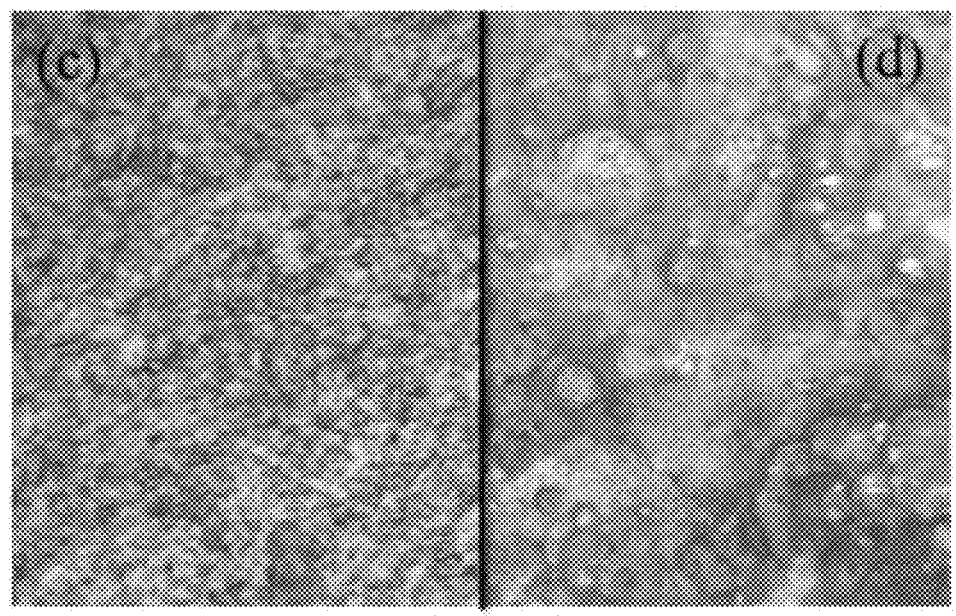
FIG. 17C shows a laser microscope substrate surface image of untreated Ti6Al4V.
FIG. 17D shows a laser microscope substrate surface image of coated Ti6Al4V.
Figures 17E, 17F:
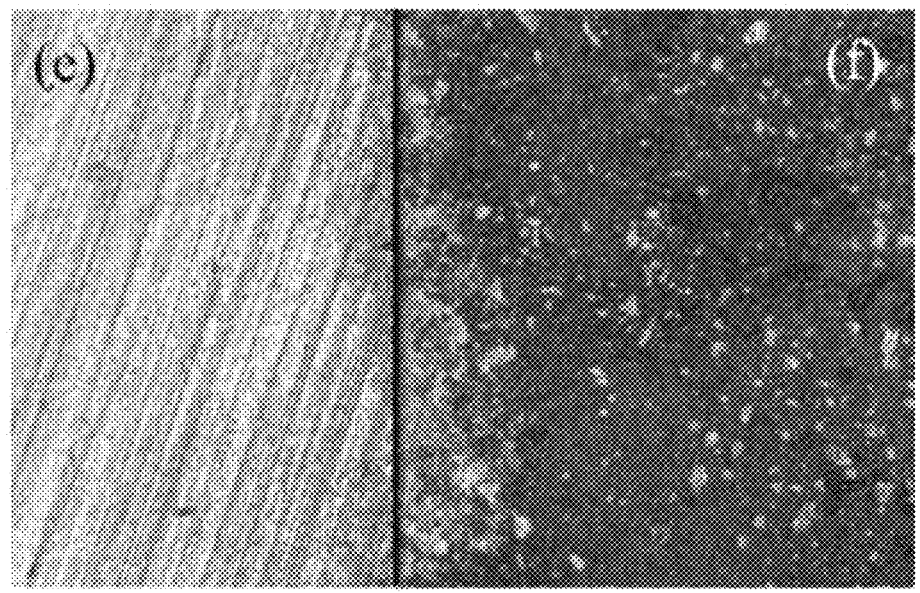
FIG. 17E shows a laser microscope substrate surface image of untreated ZTA.
FIG. 17F shows a laser microscope substrate surface image of coated ZTA.

FIGS. 17A-17H show sample surfaces before and after laser cladding, a treatment which increased the surface roughness of all samples. The roughness of the LDPE plate prepared surface finishing was initially in the range of Ra=0.30±0.02 μm (FIG. 17A). It increased to Ra=0.81±0.28 μm after treatment (FIG. 17B).

In the case of Ti6Al4V, the initial surface roughness of Ra=0.63±0.09 μm (FIG. 17C) increased to Ra=11.23±1.11 μm (FIG. 17D), a value much higher than that measured on either ceramic substrate. This effect was caused by localized melting of the Ti6Al4V substrate, which resulted in an alteration of the coating-substrate interface morphology and the formation of an alpha phase.

In the case of ZTA, the roughness changed from Ra=1.02±0.02 μm (FIG. 17E) to Ra=4.59±1.29 μm, due to the presence of partially melted particles. This is clearly visible in FIG. 17F.

Figures 17G, 17H:
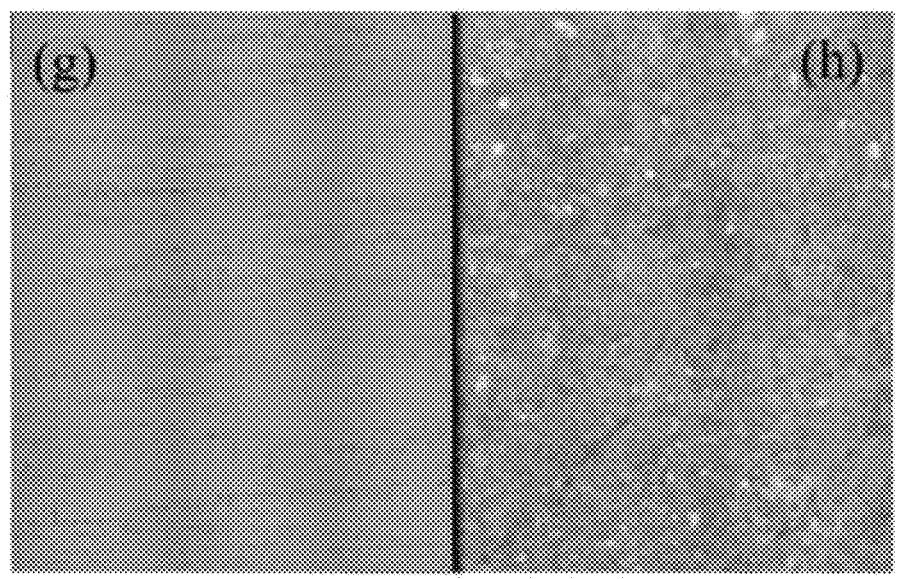
FIG. 17G shows a laser microscope substrate surface image of untreated Y-TZP.
FIG. 17H shows a laser microscope substrate surface image of coated Y-TZP.

Because the Y-TZP test bars were polished prior to laser cladding, their initial surface roughness was lower, Ra=0.02±0.01 μm (FIG. 17G). This increased to Ra=1.27±0.42 μm after laser treatment (FIG. 17H).

Figures 18A, 18B:
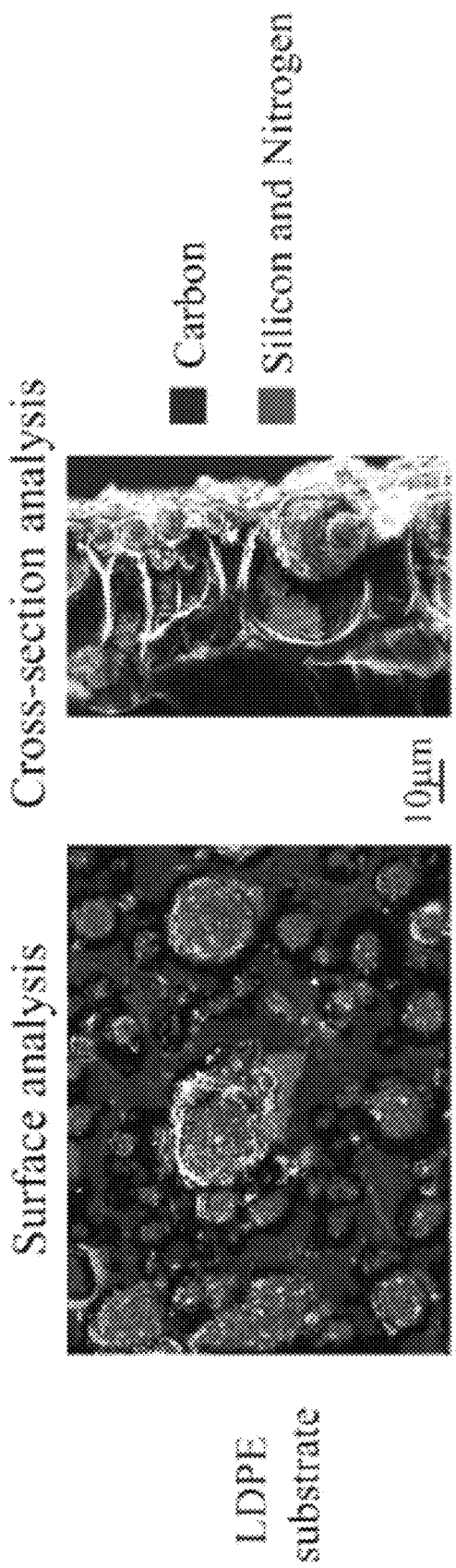
FIG. 18A shows a SEM secondary electron image overlapped with an EDS compositional maps for an LDPE surface analysis.
FIG. 18B shows a SEM secondary electron image overlapped with an EDS compositional maps for an LDPE cross-section analysis.

On the LDPE substrate, the LDPE matrix under the $Si_3N_4$ cladding (FIG. 18A) and on the cross-section images (FIG. 18B), as well as the $Si_3N_4$ particle penetration inside the LDPE matrix, are visible. Since the silicon nitride particles have a higher absorbance at 1064 nm when compared to LDPE, the ceramic particles heat up and locally melt the polymeric substrate, resulting in the incorporation of silicon nitride into LDPE. As a result, at 225 V the heated particles melt LDPE (at about 120° C.) without causing visible decomposition, which occurs between 350 and 450° C.

On the Ti6Al4V substrate, the silicon nitride coating is more homogeneous, as observed in FIG. 18C. The blue signal (titanium) is still present, but when mixed with the other elements, it changes to a lavender color. On the cross-section of the Ti6Al4V sample (FIG. 18D), it is possible to distinguish between the substrate and the cladded layers. Only occasional formation of Si—Ti intermetallics (see arrow) is evident. Moreover, the coating is composed of two different phases: a silicon-rich (red) layer with a metallic appearance, and a layer with fine dispersion of $Si_3N_4$ crystals (green) where the nitrogen signal is still intense.

Figures 18E, 18F, 18G:
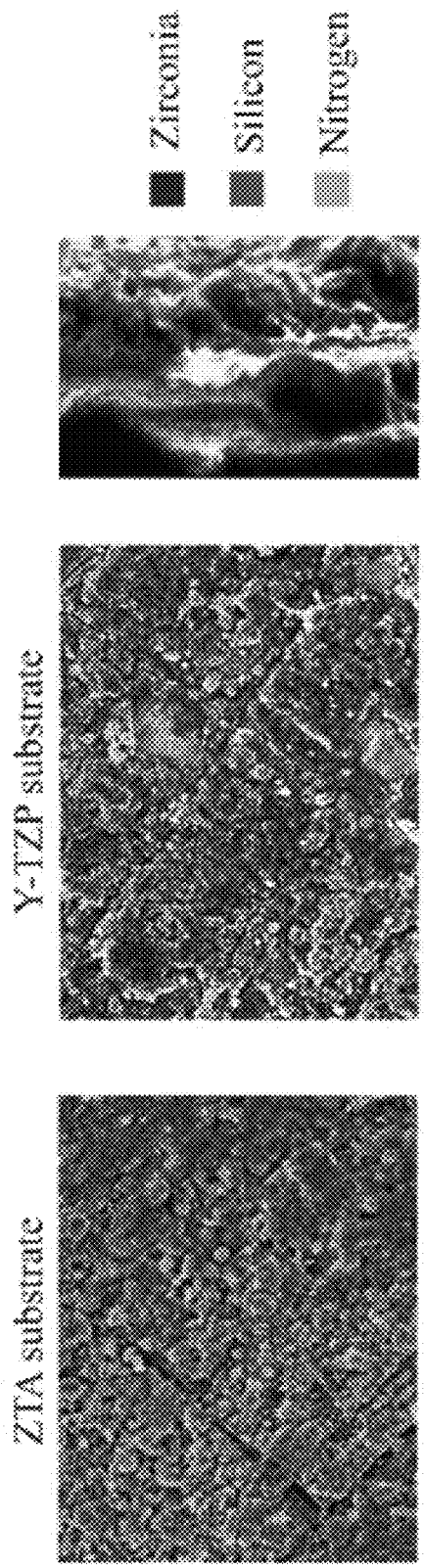
FIG. 18E shows a SEM secondary electron image overlapped with an EDS compositional maps for a ZTA surface analysis.
FIG. 18F shows a SEM secondary electron image overlapped with an EDS compositional maps for Y-TZP surface analysis.
FIG. 18G shows a SEM secondary electron image overlapped with an EDS compositional maps for a Y-TZP cross-section analysis.

Laser cladding on ceramic substrates resulted in coatings with a similar morphology, composed of partially melted silicon grains (FIGS. 18E and 18F). Due to the high melting point and low surface roughness of the ZTA and Y-TZP substrates, the cladded layer did not strongly bond with the substrate, resulting in partial delamination. Previously, an increase in bonding strength was observed when the substrates were pre-scratched using a diamond tip pen. The cross-section image (FIG. 18G) of a Y-TZP pre-scratched substrate shows a homogeneous layer when compared to both the LDPE and the Ti6Al4V substrates.

Laser treatment converted silicon nitride powder into a silicon phase and also into an amorphous phase. Laser cladding changes the morphology of the substrates to which it is applied, but the final roughness values seem more dependent on the physical properties of the material and applied power than on initial surface roughness. For example, two samples with a similar initial surface roughness, Ti6Al4V and zirconia-toughened alumina (ZTA), showed completely different morphology after treatment. However, initial surface roughness did play a role in cladded layer adhesion, as was observed by comparing the ZTA (rough) and pure zirconia (polished) images. Initially, smooth surfaces resulted in partial delamination of the coating. The applied power may also be correlated with the composition of the cladded layer: higher values resulted in a lower retained nitrogen.

Figure 19A:
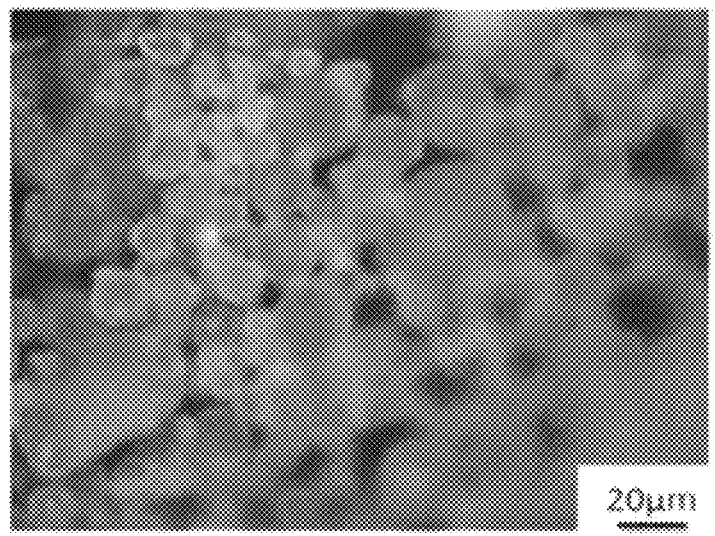
FIG. 19A shows an optical morphology of the surface of an LDPE substrate with silicon nitride particles.
Figure 19B:
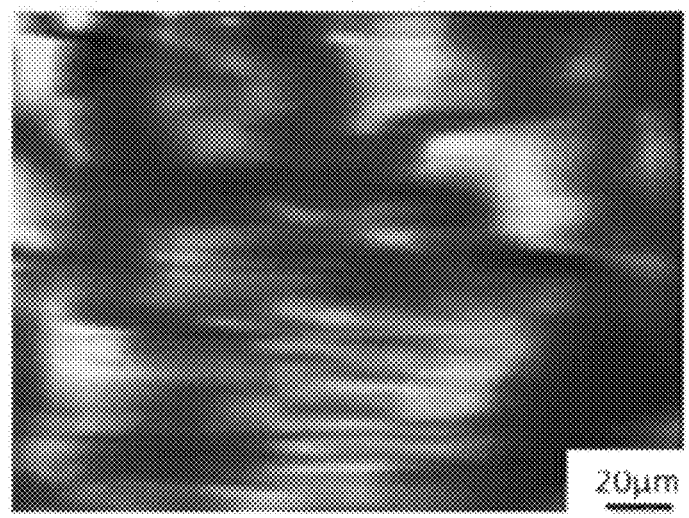
FIG. 19B shows a Raman imaging map of the surface of an LDPE substrate with silicon nitride particles.
Figure 19C:
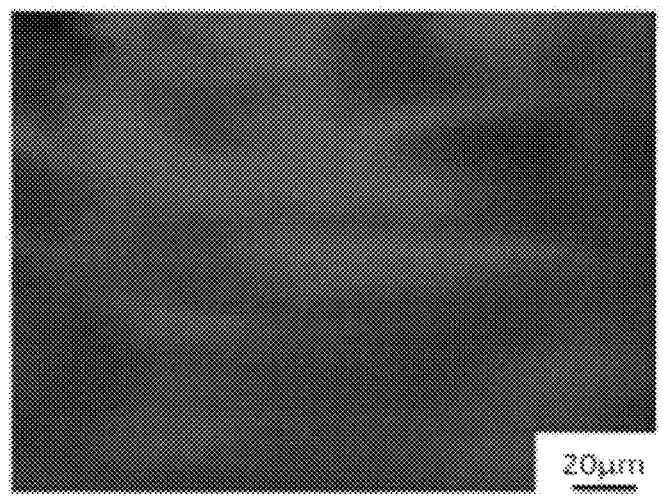
FIG. 19C shows a Raman imaging map of the surface of an LDPE substrate with silicon nitride particles.
Figure 19D:
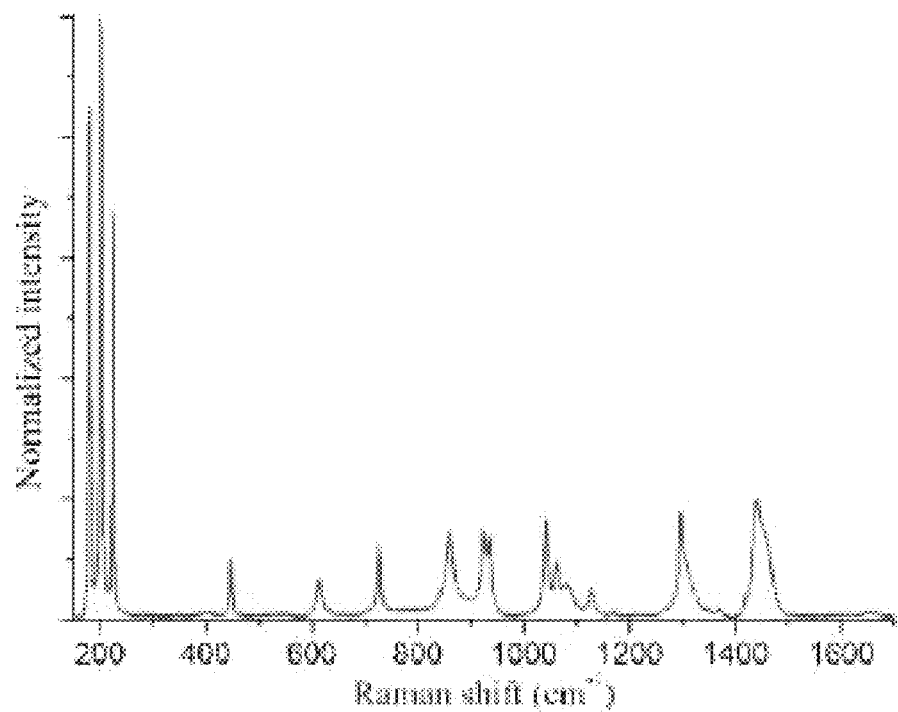
FIG. 19D shows a Raman spectra of a silicon nitride coated LDPE substrate.

FIGS. 19A-19D show the Raman maps acquired on the LDPE substrate coated with silicon nitride powders. FIG. 19A presents the optical morphology of the surface, with clearly visible silicon nitride particles. The color images were obtained by deconvolution of the Raman signal; FIG. 19B (the yellow map) represents the distribution of the LDPE phase (based on the band at 1300 cm−1) and FIG. 19C (the red map), that of silicon nitride (based on the band at 200 cm−1). The Raman spectra (FIG. 19D) confirmed the presence of silicon nitride particles in the 520 cm$^{-1}$ region. This was related to the Si—Si bonds. It also confirmed that the composition of the silicon nitride particles was essentially stoichiometric.

Figure 20A:
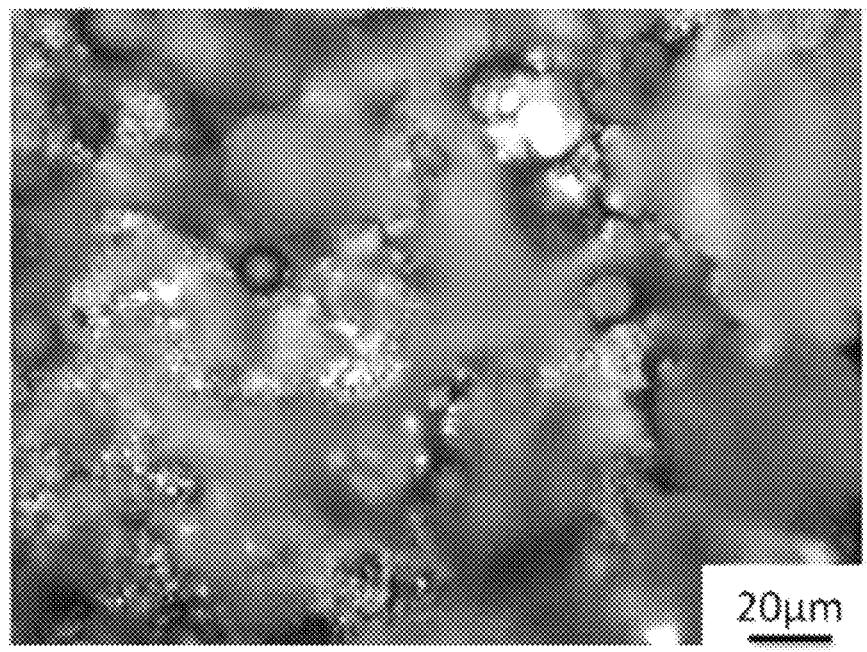
FIG. 20A shows an optical morphology of the surface of a Ti6Al4V substrate with silicon nitride particles.
Figure 20B:
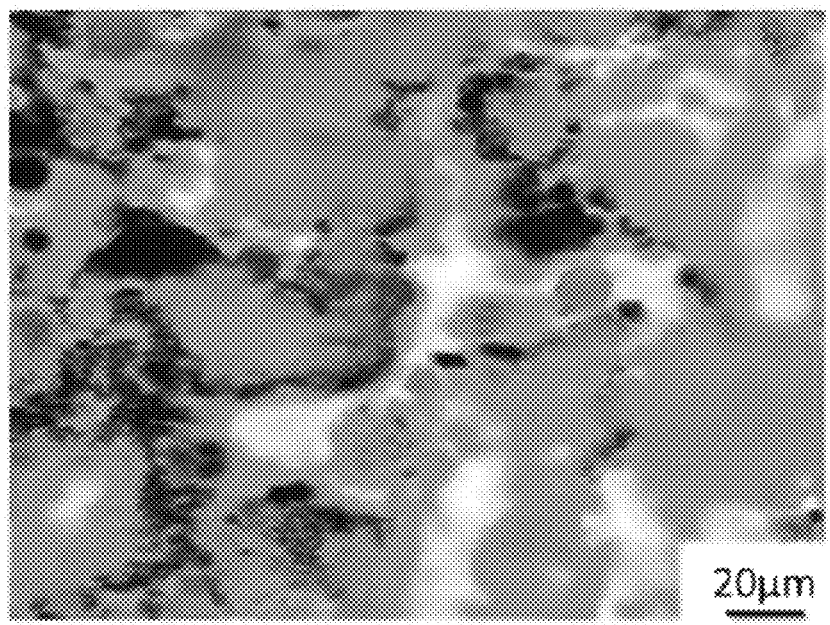
FIG. 20B shows a Raman imaging map of the surface of a Ti6Al4V substrate with silicon nitride particles.
Figure 20C:
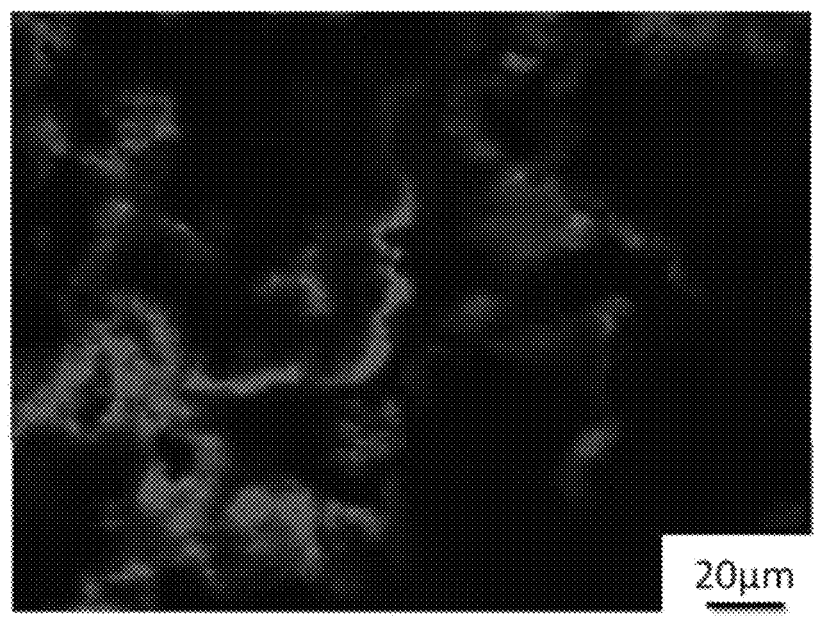
FIG. 20C shows a Raman imaging map of the surface of a Ti6Al4V substrate with silicon nitride particles.
Figure 20D:
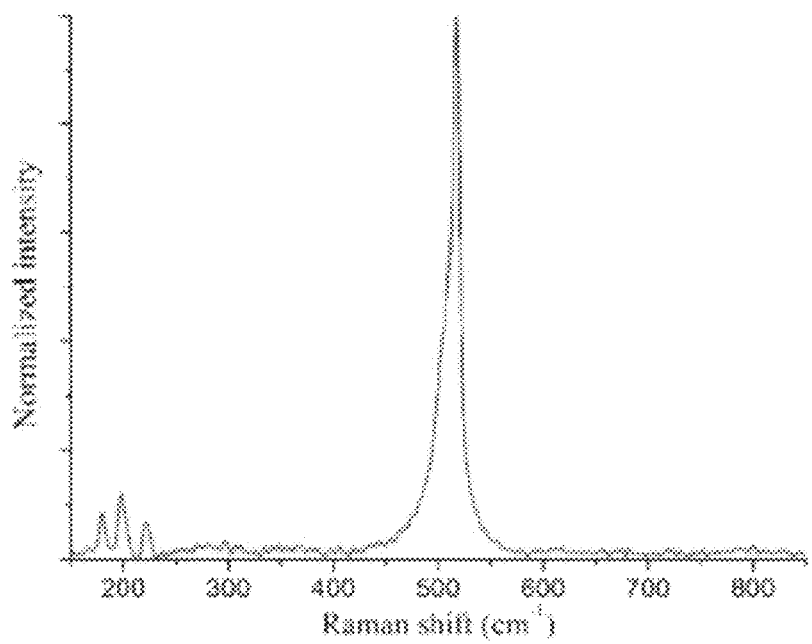
FIG. 20D shows a Raman spectra of a silicon nitride coated Ti6Al4V substrate.

FIGS. 20A-20D show the Raman imaging results acquired on the Ti6Al4V substrate. In this case, the silicon nitride powders underwent degradation during the laser cladding process. FIG. 20A (the blue and green image) shows the distribution of the amorphous silicon phase (shoulder at about 495 cm$^{-1}$) and the crystalline silicon phase (at about 520 cm$^{-1}$) (FIG. 20D). FIG. 20C (red image) shows the regions in which the silicon nitride phase is still present, as estimated by the presence of triplet peaks at about 200 cm$^{-1}$ (FIG. 20D). The red areas correspond to optical image regions in which small silicon nitride crystals are clearly visible.

Figure 21A:
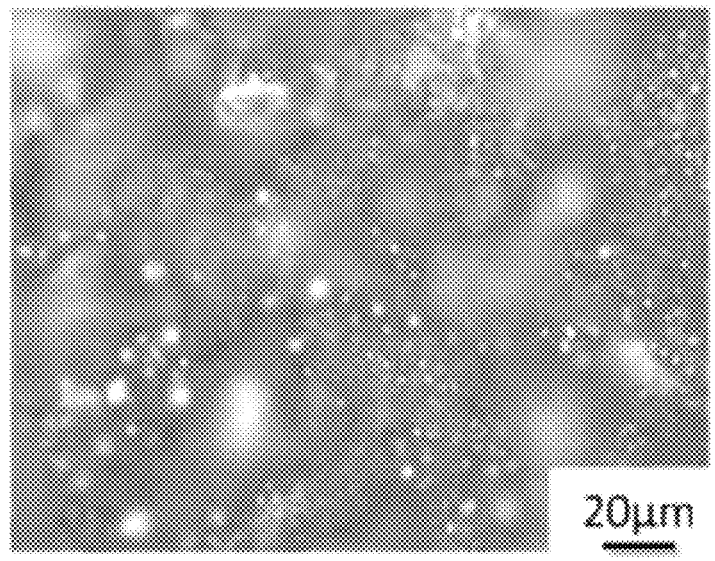
FIG. 21A shows a Raman imaging map of the surface of a ZTA substrate with silicon nitride particles.
Figure 21B:
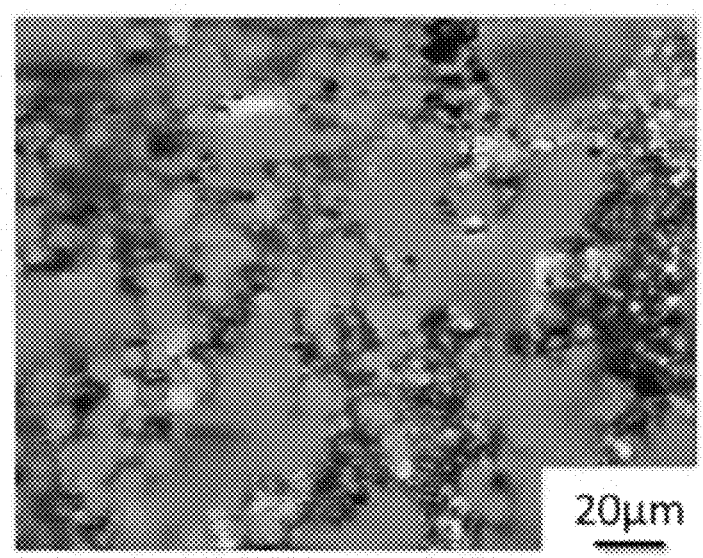
FIG. 21B shows a Raman imaging map of the surface of a ZTA substrate with silicon nitride particles.
Figure 21C:
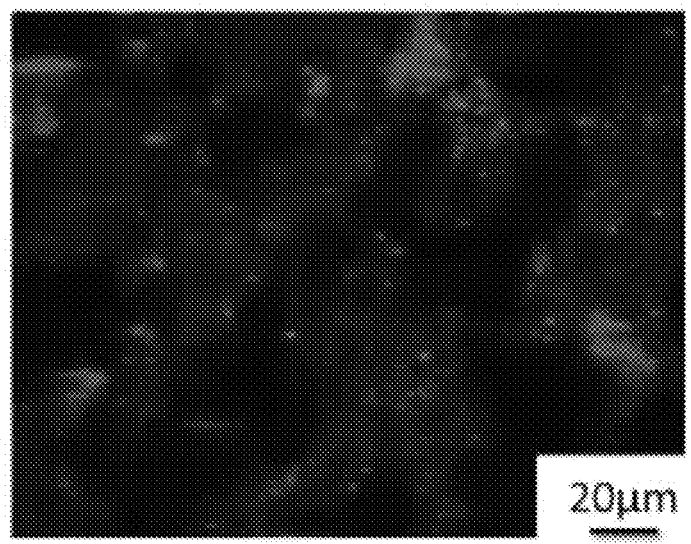
FIG. 21C shows a Raman imaging map of the surface of a ZTA substrate with silicon nitride particles.
Figure 21D:
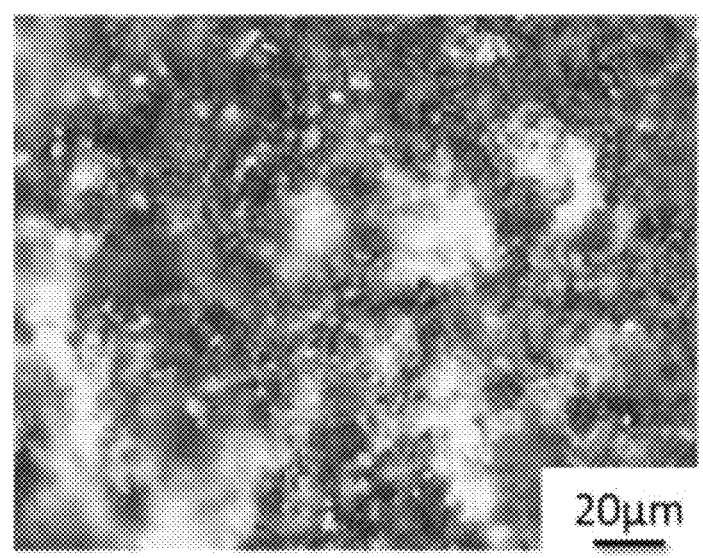
FIG. 21D shows a Raman imaging map of the surface of a Y-TZP substrate with silicon nitride particles.
Figure 21E:
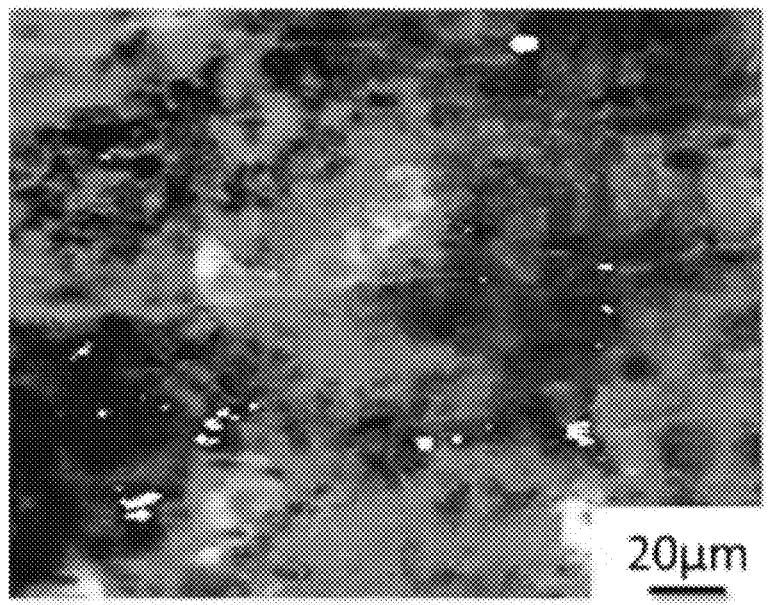
FIG. 21E shows a Raman imaging map of the surface of a Y-TZP substrate with silicon nitride particles.
Figure 21F:
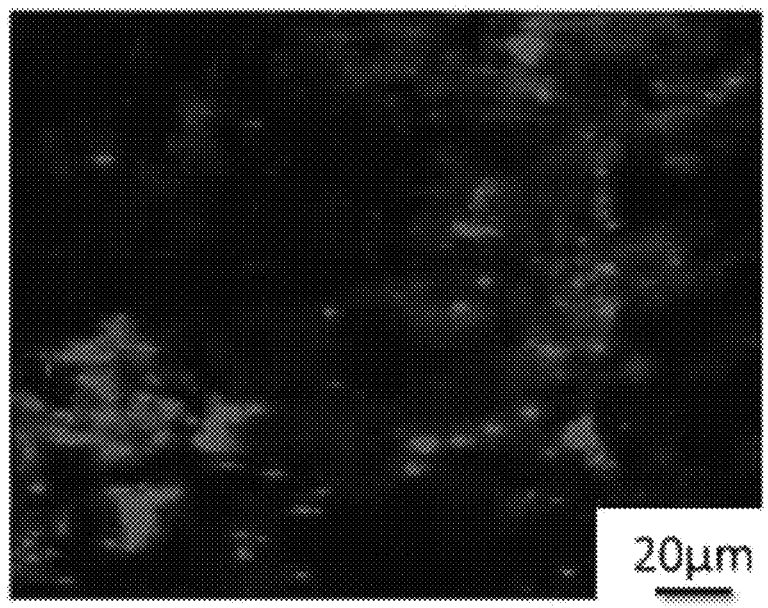
FIG. 21F shows a Raman imaging map of the surface of a Y-TZP substrate with silicon nitride particles.

FIGS. 21A-21F shows the Raman imaging results obtained on the two ceramic substrates. For both materials, the blue/green compositional maps (FIGS. 21B and 21E) show amorphous and crystalline silicon signals, covering the entire surface. In the case of ZTA, the two phases are equally dispersed, with about a 60% amorphous signal, while for Y-TZP the crystalline phase is localized in a few spots, with a 80% amorphous phase. Both materials showed stoichiometrically-similar residual $Si_3N_4$ particle dispersion (FIGS. 21C and 21F).

Raman spectroscopic images obtained for the different substrates showed the appearance of a strong signal at about 520 cm$^{-1}$ related to the presence of Si—Si bonds formed due to the release of nitrogen from the surface. Depending on the position on the spectra, the Si—Si bonds may be associated with the presence of amorphous or nanocrystalline silicon, the latter being more abundant at higher power settings.

Figure 22:
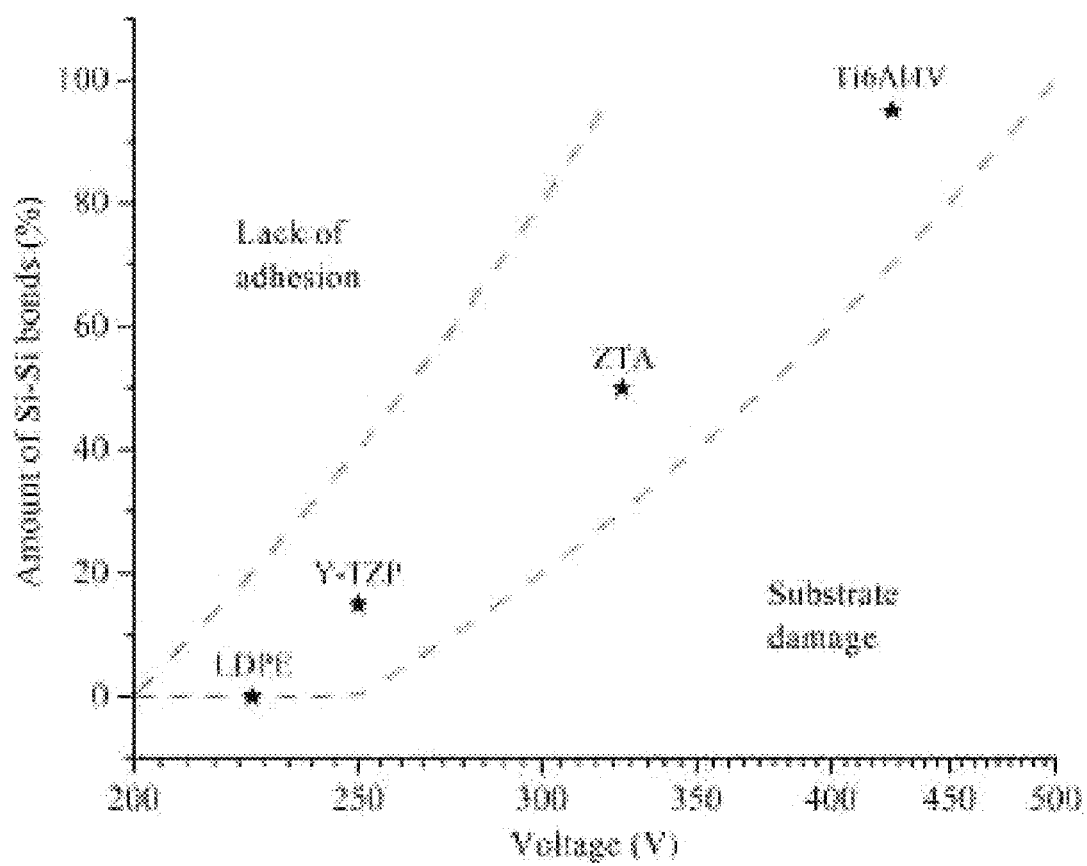
FIG. 22 is a qualitative representation of the applied voltage/Si—Si bond relationship measured by X-ray Photoelectron Spectroscopy, as an indicator of substrate chemical composition.

FIG. 22 shows a qualitative Si—Si bond dependency (measured by XPS), with respect to the applied power for each material. If the applied power is under a certain threshold, the coating does not adhere to the substrate and the powder is scattered by the laser beam. The threshold is dependent on the physical properties of the materials, such as melting point and absorbance coefficient. Cladding of the polymer was achieved at relatively low power levels, due to the melting of the matrix. This results in a virtually stoichiometric coating. In the case of ceramics, the coating required higher applied power to be deposited, but the stoichiometry of the coating changed into a silicon-rich phase. Although metals also require high power to attach the ceramic coating to the surface, this power melts the metallic substrate with the formation of a high content silicon-rich coating.

Biological Testing

The antibacterial study pf the samples used gram-positive *S. epidermidis*. *Staphylococcus epidermidis* (14990®ATCC™) cells were cultured in heart infusion (HI) broth at 37° C. for 18 h and titrated by colony-forming assay using brain heart infusion (BHI) agar. Aliquots of $1\times10^7$ bacteria were diluted in 10 µL of phosphate-buffered saline (PBS) at physiological pH and ionic strength. The samples underwent preliminary UV sterilization and were distributed into wells. To each well, 1 mL of bacteria culture was added, and samples were incubated at 37° C. under aerobic conditions for 12, 24, and 48 h.

Cell viability was evaluated using a tetrazolium-based assay from a microbial viability assay kit (WST-8). Substrates with *Staphylococcus epidermidis* were collected at 24 and 48 h after cultivation and soaked in 1000 µL of PBS in 12-well plates. WST-8 solution was added to each well and Optical Density (OD) values were measured (the absorbance at 490 nm) using a plate reader EMax after incubation for 30-60 min.

SaOS-2 human osteosarcoma cells were used to test for osteoconductivity. They were first cultured and incubated in 4.5 g/L glucose DMEM (D-glucose, L-glutamine, phenol red, and sodium pyruvate) supplemented with 10% fetal bovine serum. They were allowed to proliferate within Petri dishes for about 24 h at 37° C. The final SaOS-2 concentration was $5\times10^5$ cell/mL. The cultured cells were then deposited on the top surface of samples previously sterilized by exposure to UV-C light for 30 min. In osteoconductivity tests, cell seeding took place in an osteogenic medium which consisted of DMEM supplemented with about 50 pig/mL ascorbic acid, 10 mM 13-glycerol phosphate, 100 mM hydrocortisone, and ~10% fetal bovine calf serum. The samples were incubated up to 14 days at 37° C. The medium was changed twice a week during the incubation period. Subsequently, the cells were stained for fluorescence microscopy with green dye to identify osteocalcin (Monoclonal, Clone 5-12H, dilution 1:500) and red dye to show osteopontin (Osteopontin, O-17, Rabbit IgG, 1:500).

After exposure to osteoblasts, each batch of samples was observed using fluorescence microscopy (BZ-X700). Prior to examination, the sample surfaces were treated with different immunostaining reagents, including Hoechst 33,342, anti-Human Osteocalcin Clone2H9F11F8, and Isotype IgG, Rabbit polyclonal antibody. Hoechst 33,342, a cell nucleus stain (DAPI 4',6-Diamidino-2-phenylindole, dihydrochloride, solution), served to visualize cell proliferation, while the other two antibodies were used to stain mineralization and bone matrix formation concentration quantifying the matrix proteins osteocalcin and osteopontin, respectively. Subsequently, a secondary antibody, Goat anti-Mouse IgG1 Antibody FITC Conjugated was added to enhance signal detection and visualization.

Figure 23A:
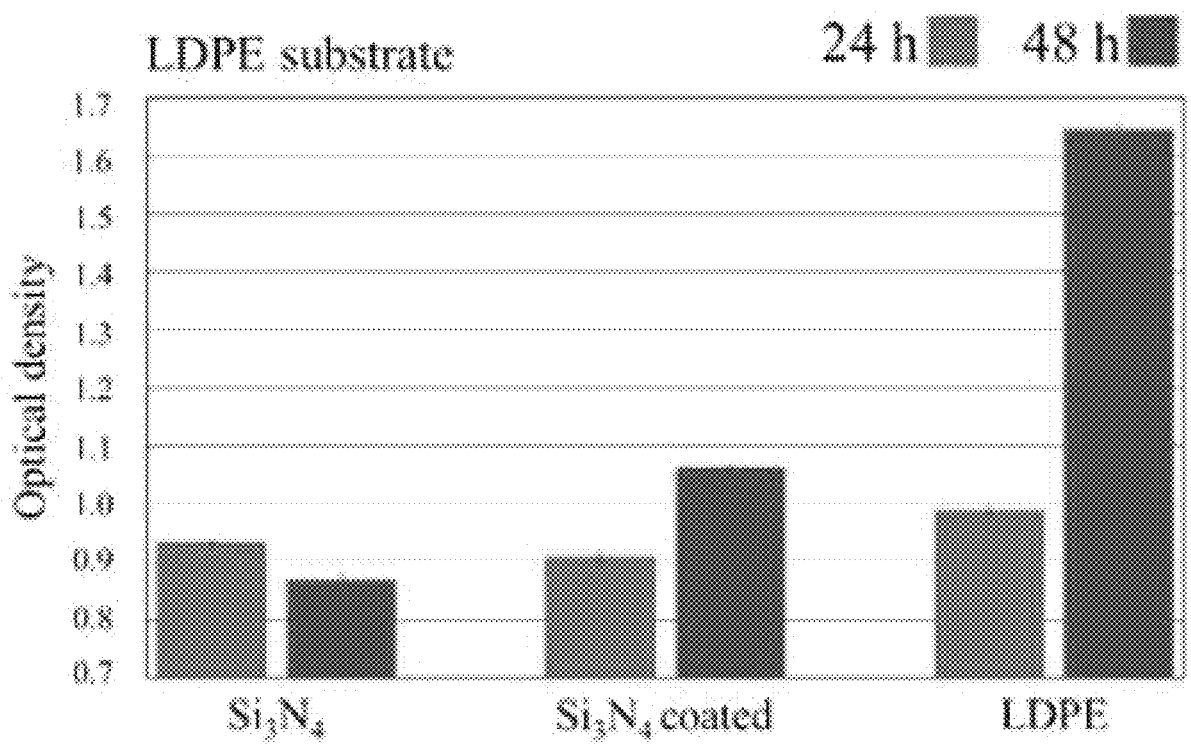
FIG. 23A shows microbial viability assays (WST) of *Staphylococcus epidermidis* as an indicator of bacterial exposure time for silicon nitride coated and uncoated LDPE substrates.
Figure 23B:
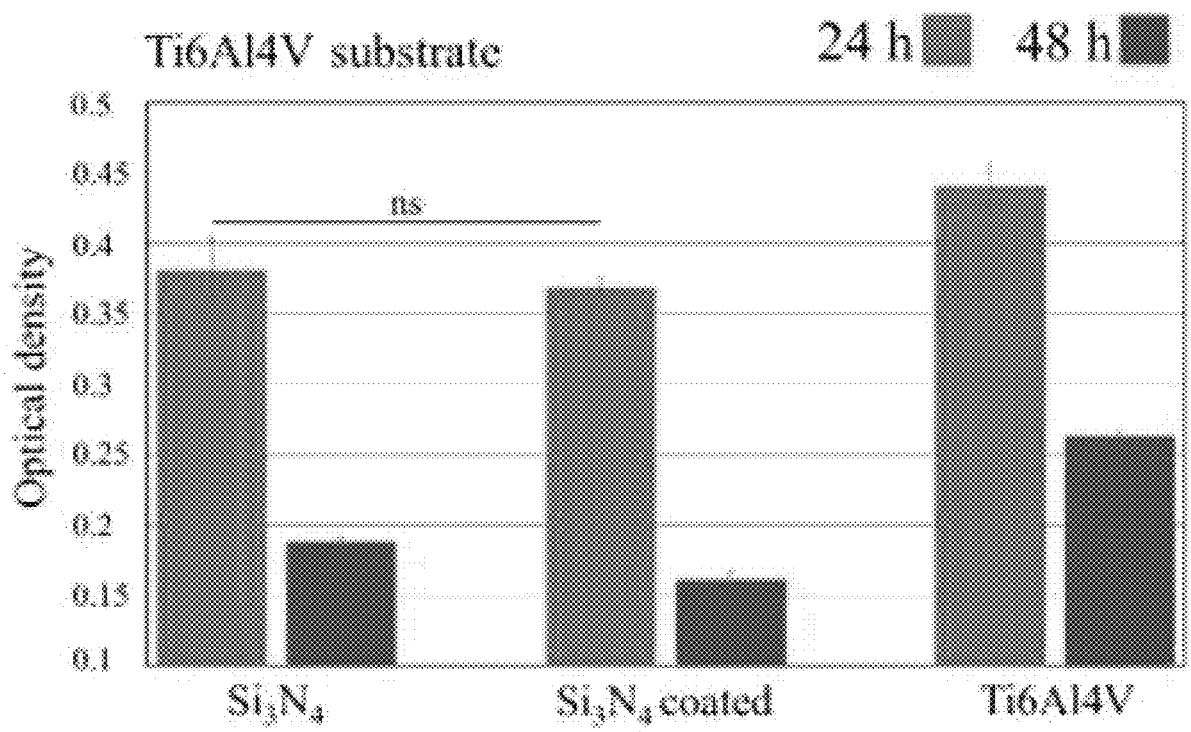
FIG. 23B shows microbial viability assays (WST) of *Staphylococcus epidermidis* as an indicator of bacterial exposure time for silicon nitride coated and uncoated Ti6Al4V substrates.
Figure 23C:
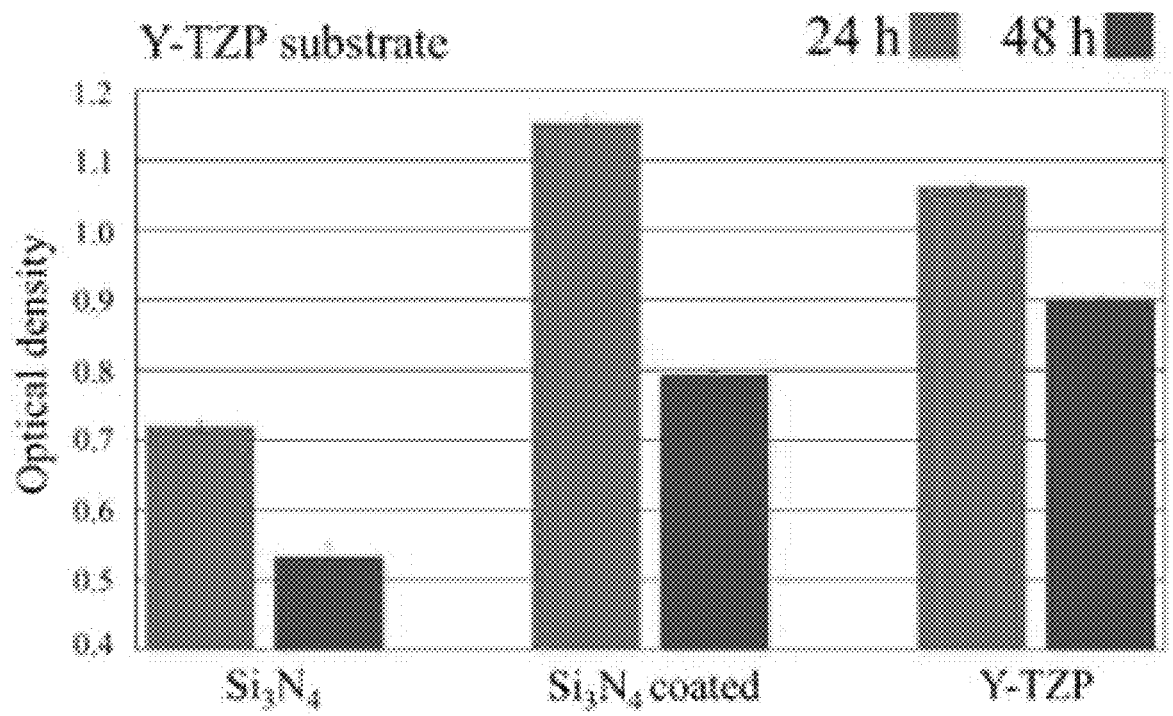
FIG. 23C shows microbial viability assays (WST) of *Staphylococcus epidermidis* as an indicator of bacterial exposure time for silicon nitride coated and uncoated Y-TZP substrates.

FIGS. 23A-23C show the microbial viability assays (WST) for three of the four substrates, compared with those of bulk silicon nitride and an untreated reference.

It was observed that $Si_3N_4$ reference samples usually displayed the lowest optical density at 48 h, with the exception of the Ti6Al4V substrate where its performance was comparable to that of the coated sample. The biological effects of silicon nitride were time-dependent and reach their maximum after about 12 h of treatment.

In the case of LDPE substrates, the trend observed for $Si_3N_4$ is the same, but on polymer and composite substrates, it changed completely. $Si_3N_4$ bulk is the only sample which showed that bacterial viability decreased over time. The LDPE substrates exhibit a growth of more than 60% in OD between 24 and 48 h possessing the highest bacterial amount in both the times. Despite the lowest OD value presenting at 24 h, the $Si_3N_4$-coated samples showed a slight variation, even if lower than that of the negative control.

In the case of Ti6Al4V, the microbial viability assay at 24 h showed a higher bacterial count on the Ti6Al4V uncoated sample than on identical uncoated or coated $Si_3N_4$ samples. At 48 h, a decreasing trend of OD was detected on all substrates. However, the $Si_3N_4$-coated substrate had the lowest OD value when compared with the two other bulk samples.

For zirconia samples (ZTA and Y-TZP show similar results), the silicon nitride coated samples treated with *S. epidermidis* had the highest 24-h living bacteria count. However, the lytic efficacy improved progressively with time. At 48 h, the optical density of the bacteria was 60% higher than on silicon nitride, but lower than on Y-TZP.

The fluorescence microscopy images obtained for various samples showed increased bone tissue production for the laser-cladded surfaces when compared to the uncoated substrates, as evidenced by both osteocalcin and osteopontin distributions.

Figures 24A, 24B, 24C:
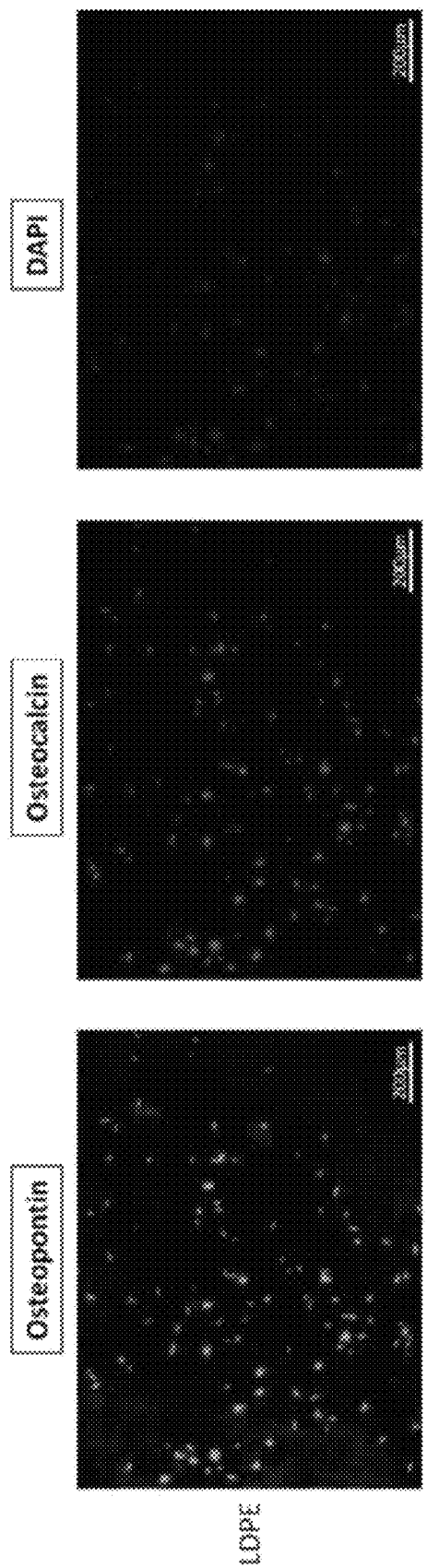
FIG. 24A is a fluorescence micrograph of a LDPE sample showing osteocalcin after exposure to SaOS-2 cells.
FIG. 24B is a fluorescence micrograph of a LDPE sample showing osteopontin after exposure to SaOS-2 cells.
FIG. 24C is a fluorescence micrograph of a LDPE sample showing nuclei after exposure to SaOS-2 cells.
Figure 24F:
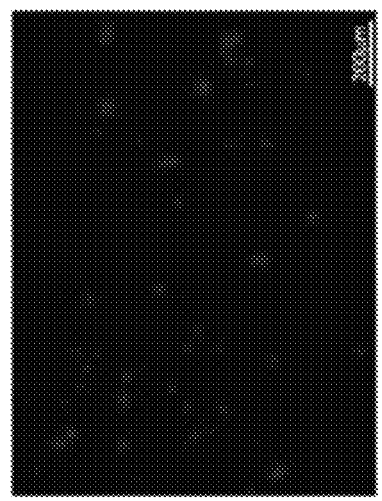
FIG. 24F is a fluorescence micrograph of a silicon nitride coated LDPE sample showing nuclei after exposure to SaOS-2 cells.
Figure 24E:
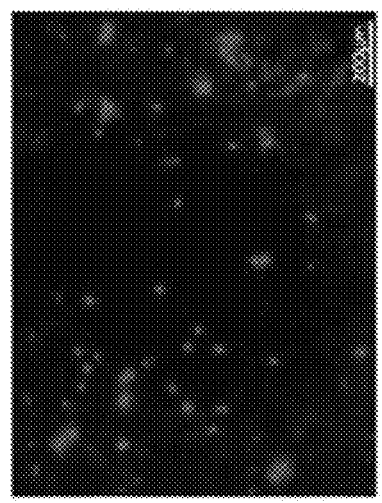
FIG. 24E is a fluorescence micrograph of a silicon nitride coated LDPE sample showing osteopontin after exposure to SaOS-2 cells.
Figure 24D:
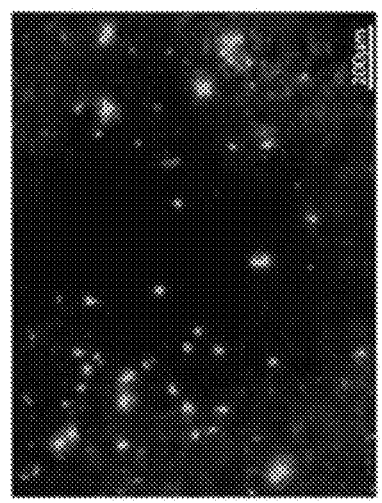
FIG. 24D is a fluorescence micrograph of a silicon nitride coated LDPE sample showing osteocalcin after exposure to SaOS-2 cells.

FIGS. 24A-24F show the results of the fluorescence microscopy testing with markers for nuclei (blue), osteocalcin (green), and osteopontin (red) for an LDPE substrate (FIGS. 24A-24C) and a silicon nitride coated LDPE sample (FIGS. 24D-24F). Unlike zirconia and Ti6Al4V, the uncoated LDPE substrates appear to be colonized by cells and coating application does not significantly affect the amount or distribution of either cell nuclei or bone tissue.

Figure 25F:
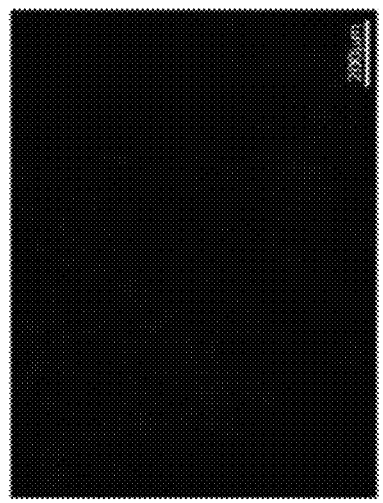
FIG. 25F is a fluorescence micrograph of a silicon nitride coated Ti6Al4V sample showing nuclei after exposure to SaOS-2 cells.
Figure 25E:
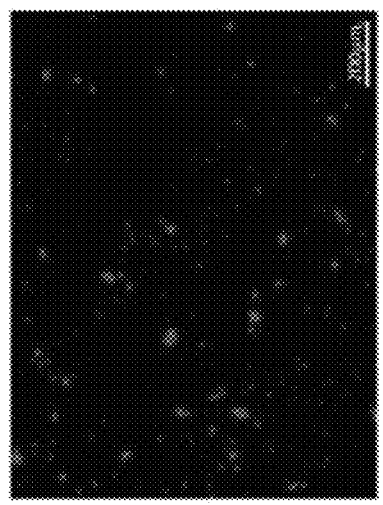
FIG. 25E is a fluorescence micrograph of a silicon nitride coated Ti6Al4V sample showing osteopontin after exposure to SaOS-2 cells.
Figure 25D:
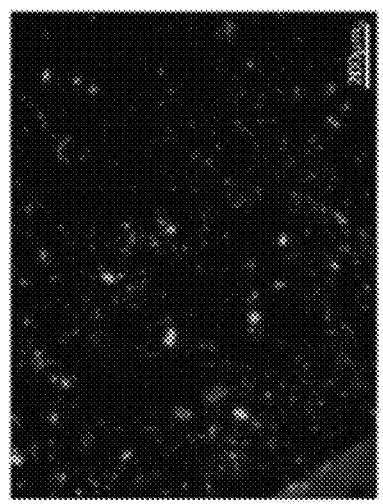
FIG. 25D is a fluorescence micrograph of a silicon nitride coated Ti6Al4V sample showing osteocalcin after exposure to SaOS-2 cells.

FIGS. 25A-25F show the results of the fluorescence microscopy testing with markers for nuclei (blue), osteocalcin (green), and osteopontin (red) for a Ti6Al4V alloy substrate (FIGS. 25A-25C) and a silicon nitride coated Ti6Al4V sample (FIGS. 25D-25F). It was observed that cell nuclei are not homogeneously distributed on the sample surface, forming agglomerates at the center where bone tissue (osteopontin and osteocalcin) also formed. Coated samples, on the other hand, were homogeneously covered.

Figures 26A, 26B, 26C:
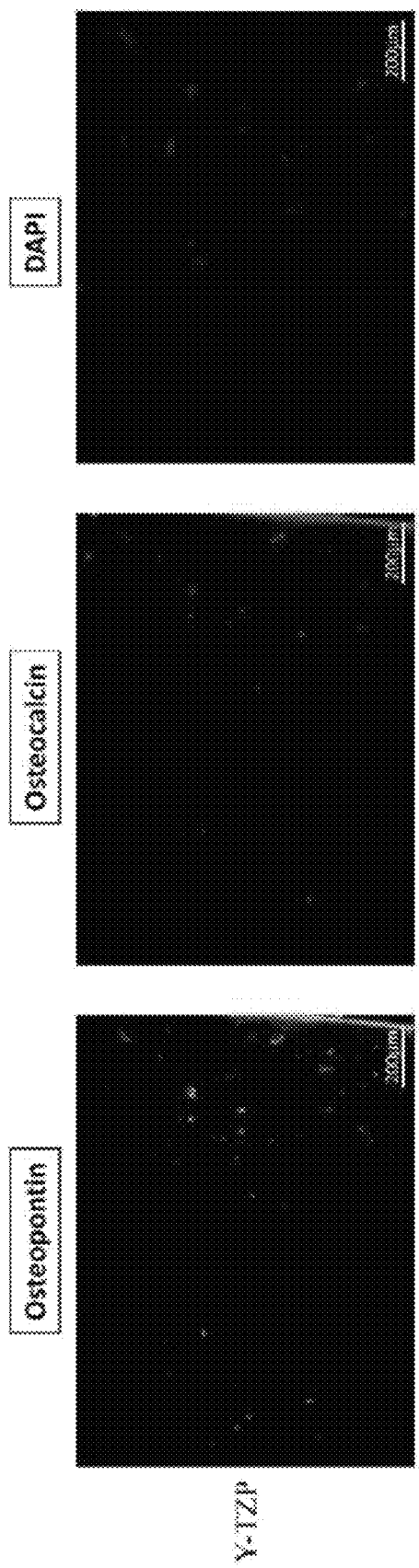
FIG. 26A is a fluorescence micrograph of a Y-TZP sample showing osteocalcin after exposure to SaOS-2 cells.
FIG. 26B is a fluorescence micrograph of a Y-TZP sample showing osteopontin after exposure to SaOS-2 cells.
FIG. 26C is a fluorescence micrograph of a Y-TZP sample showing nuclei after exposure to SaOS-2 cells.
Figures 26D, 26E, 26F:
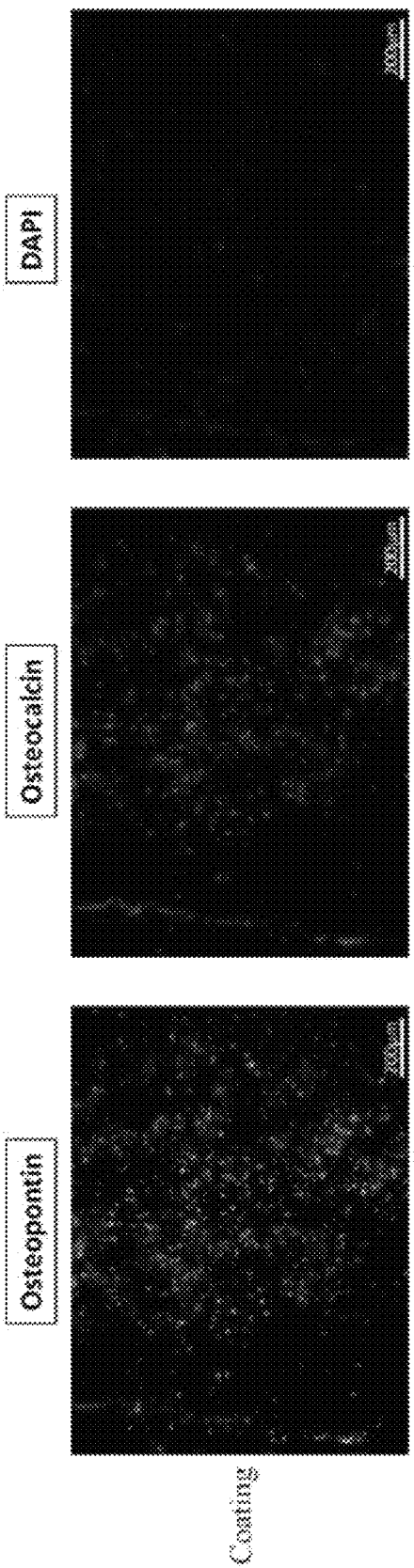
FIG. 26D is a fluorescence micrograph of a silicon nitride coated Y-TZP sample showing osteocalcin after exposure to SaOS-2 cells.
FIG. 26E is a fluorescence micrograph of a silicon nitride coated Y-TZP sample showing osteopontin after exposure to SaOS-2 cells.
FIG. 26F is a fluorescence micrograph of a silicon nitride coated Y-TZP sample showing nuclei after exposure to SaOS-2 cells.

FIGS. 26A-26F show the results of the fluorescence microscopy testing with markers for nuclei (blue), osteocalcin (green), and osteopontin (red) for a Y-TZP substrate (FIGS. 26A-26C) and a silicon nitride coated Y-TZP sample (FIGS. 26D-26F). ZTA and Y-TZP show similar results. On the uncoated substrate, three signals for the non-collagenous bone matrix proteins in osteoblasts were observed: osteocalcin, osteopontin, and for cell nuclei. All were barely visible and only localized in a few spots. Moreover, the increased distribution of blue DAPI signals indicates that more nuclei than bone tissue formed. When the coating was applied, osteopontin and osteocalcin were strengthened and more uniformly distributed over the entire area.

Figure 27A:
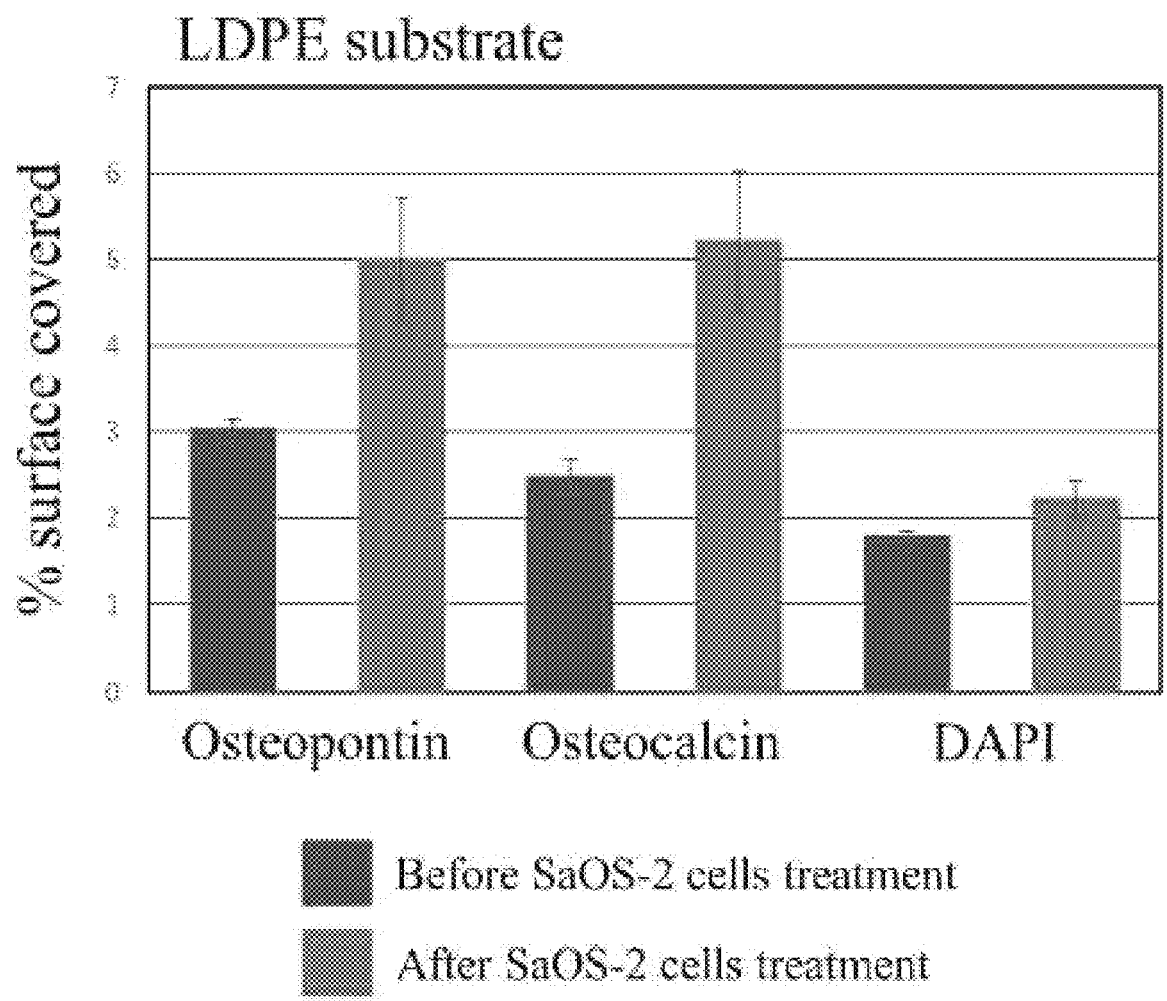
FIG. 27A shows relative surface substrate amounts assigned to the fluorescent probes used for osteocalcin, osteopontin, and cell nuclei based on fluorescence micrograph images of LDPE substrates before and after treatment.
Figure 27B:
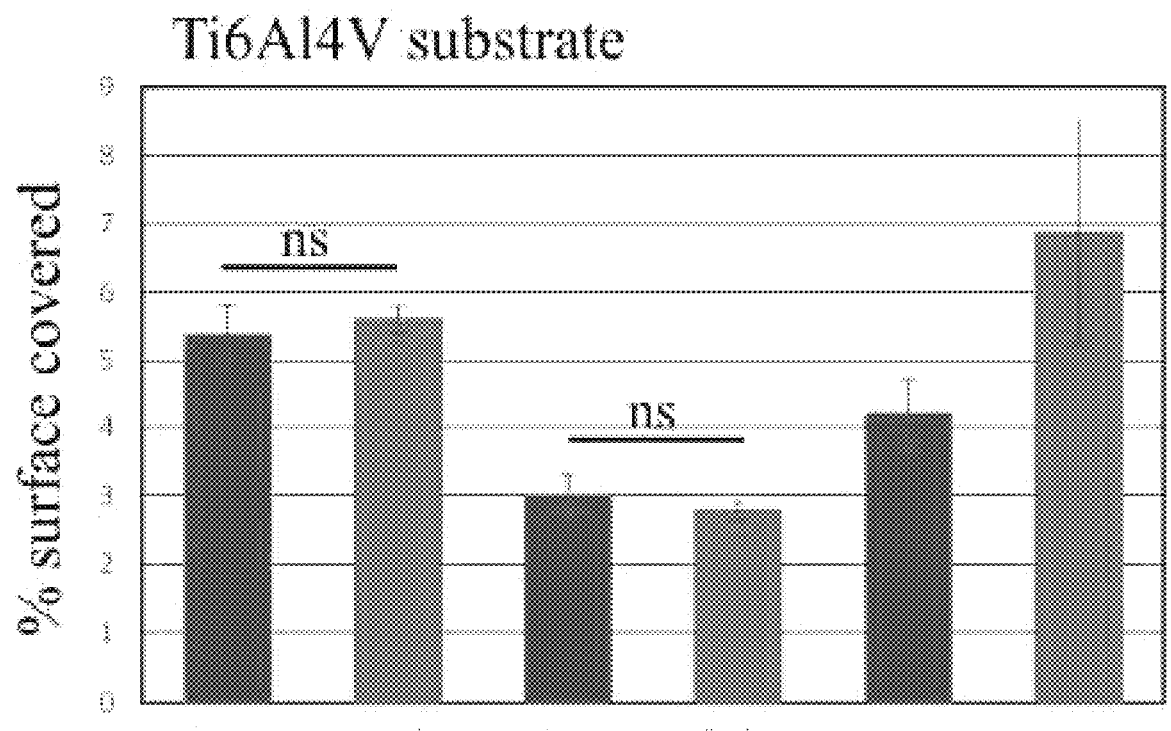
FIG. 27B shows relative surface substrate amounts assigned to the fluorescent probes used for osteocalcin, osteopontin, and cell nuclei based on fluorescence micrograph images of Ti6Al4V substrates before and after treatment.
Figure 27C:
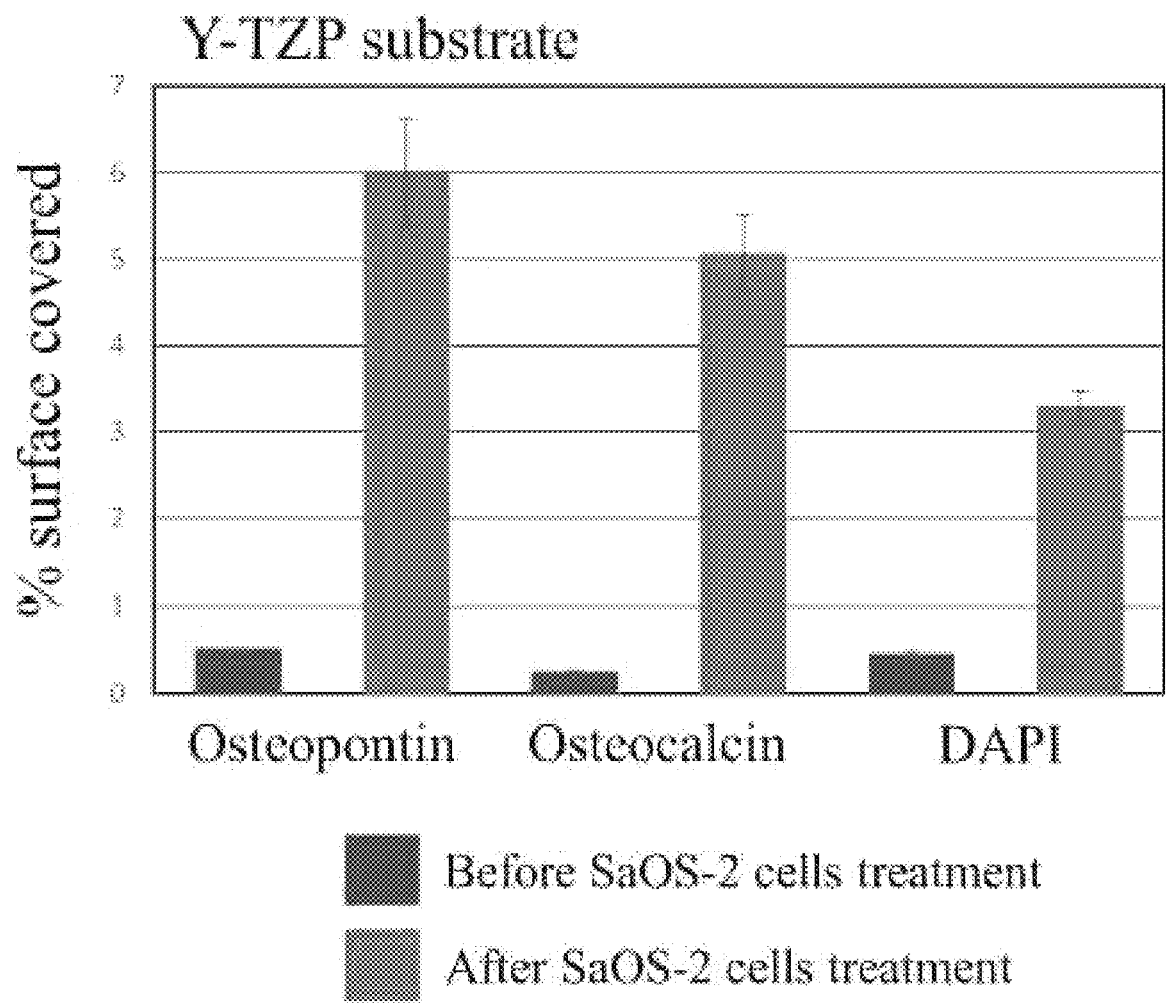
FIG. 27C shows relative surface substrate amounts assigned to the fluorescent probes used for osteocalcin, osteopontin, and cell nuclei based on fluorescence micrograph images of Y-TZP substrates before and after treatment.

FIGS. 27A-27C show the fluorescence analysis of substrate surface bone and cell nuclei before and after treatment. For the LDPE substrate, the bone tissue increased around 2%, but the percentage of cell nuclei still present on the surface was nearly identical to that of the untreated substrate. For the Ti6Al4V, the number of nuclei was higher than that of the untreated samples, but bone formation was virtually the same for both samples. For the Y-TZP substrate, the histogram confirmed a higher amount of surface bone tissue formation. An increase of 5-6% of the bone product and 3% of nuclei on the coated surface was evident.

The in vitro bacteria counts summarized in FIGS. 27A-27C confirmed that all silicon nitride-based cladded layers have time-dependent antibacterial effects. The trend observed in Y-TZP- and Ti6Al4V-coated substrates showed a clear decrease over time. In the LDPE $Si_3N_4$-coated substrates, the opposite trend was observed, but the increase was less significant compared with that of uncoated LDPE. The slight increase of OD at 48 h may be associated with adopted laser treatment because, although particles were fixed without physically modifying the bulk substrates of Ti6Al4V and Y-TZP, the surface was melted by the laser. In LDPE, this resulted in $Si_3N_4$ particle incorporation. This provided a non-homogeneously $Si_3N_4$ covered surface, but areas with LDPE were still present as observed in FIGS. 18A-18B.

More bone tissue was formed on substrates with higher fractions of surface silicon phase. In silicon-rich samples, cells produced bone tissue, but at a lower rate than that of other materials.

Substrate roughness also contributed actively to bone formation. The ZTA and Ti6Al4V samples achieved higher surface roughness after laser cladding when compared to other substrates. This influenced the biological response.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of coating the surface of a biomedical implant comprising:
   providing the biomedical implant;
   roughening at least one surface of the biomedical implant;
   laser cladding a coating of silicon nitride on the at least one roughened surface, the laser cladding comprising:
      directing a laser beam to at least one roughened surface of the biomedical implant; and
      pre-applying a powder mixture or simultaneously directing the powder mixture comprising silicon nitride to the at least one roughened surface of the biomedical implant; and
   repeating the laser cladding step until the coating of silicon nitride has a thickness of at least 10 μm, wherein roughening the at least one surface of the biomedical implant comprises using free abrasive machining to form random scratches.

2. The method of claim 1, wherein the biomedical implant comprises zirconia, alumina, alumina/zirconia composites (ZTA), titanium, titanium alloys, polyethylene, polyurethane, polyetherketoneketone, or combinations thereof.

3. The method of claim 2, wherein the biomedical implant comprises yttria-stabilized zirconia.

4. The method of claim 2, wherein the biomedical implant comprises Ti6Al4V.

5. The method of claim 1, wherein the coating of silicon nitride comprises about 5 wt. % to about 15 wt. % silicon nitride.

6. The method of claim 1, wherein the silicon nitride powder comprises $\alpha$-$Si_3N_4$, $\beta$-$Si_3N_4$, $\beta$-SiYAlON, SiAlON, or SiYON.

7. The method of claim 1, wherein the powder mixture comprising silicon nitride is formed from ground acicular $\beta$-$Si_3N_4$ grains and a Si—Y—O—N grain-boundary phase.

8. The method of claim 1, wherein the random scratches are about 5 μm to 500 μm wide.

9. The method of claim 1, wherein the laser beam has a wavelength of about 1064 nm and a pulse rate of about 4 ms.

10. The method of claim 1, wherein the laser is a 100 watt picosecond laser tuned to emit nanosecond pulses at a raster speed of 5,500 mm/s, at power level of 25% and pulse widths of 200 to 500 μm, respectively, operating at 1000 kHz, a hatching distance of 0.03 mm, hatching overlap of 60.34%, at a distance of laser impact of 0.0055 mm.

11. The method of claim 1, wherein laser cladding is repeated at least three times.

12. The method of claim 1, wherein the coating of silicon nitride has a thickness of at least 15 μm.

13. The method of claim 1, wherein the laser cladding further comprises:
supplying a constant flux of nitrogen gas.

14. A biomedical implant comprising a surface coated using the method of claim 1.

15. A method of coating the surface of a biomedical implant comprising:
providing the biomedical implant;
roughening at least one surface of the biomedical implant;
laser cladding a coating of silicon nitride on the at least one roughened surface, the laser cladding comprising:
directing a laser beam to at least one roughened surface of the biomedical implant; and
pre-applying a powder mixture or simultaneously directing the powder mixture comprising silicon nitride to the at least one roughened surface of the biomedical implant; and
repeating the laser cladding step until the coating of silicon nitride has a thickness of at least 10 μm,
wherein the laser is a 100 watt picosecond laser tuned to emit nanosecond pulses at a raster speed of 5,500 mm/s, at power level of 25% and pulse widths of 200 to 500 μm, respectively, operating at 1000 kHz, a hatching distance of 0.03 mm, hatching overlap of 60.34%, at a distance of laser impact of 0.0055 mm.

16. The method of claim 15, wherein the biomedical implant comprises zirconia, alumina, alumina/zirconia composites (ZTA), titanium, titanium alloys, polyethylene, polyurethane, polyetherketoneketone, yttria-stabilized zirconia, Ti6Al4V, or combinations thereof.

17. The method of claim 15, wherein roughening the at least one surface of the biomedical implant comprises using free abrasive machining to form random scratches about 5 μm to 500 μm wide.

18. The method of claim 15, wherein the laser beam has a wavelength of about 1064 nm and a pulse rate of about 4 ms.

19. The method of claim 15, wherein the laser cladding is repeated at least three times.

20. The method of claim 15, wherein the coating of silicon nitride has a thickness of at least 15 μm.

21. The method of claim 15, wherein the laser cladding further comprises:
supplying a constant flux of nitrogen gas.

* * * * *